United States Patent [19]

Sundelin et al.

[11] Patent Number: 5,629,174

[45] Date of Patent: May 13, 1997

[54] RECOMBINANT C140 RECEPTOR

[75] Inventors: Johan Sundelin, Furulund, Sweden; Robert M. Scarborough, Belmont, Calif.

[73] Assignee: COR Therapeutics, Inc., South San Francisco, Calif.

[21] Appl. No.: 97,938

[22] Filed: Jul. 26, 1993

[51] Int. Cl.$^6$ .............................. C12P 21/02; C12N 5/10; C12N 15/63

[52] U.S. Cl. ................. 435/69.1; 435/172.3; 435/320.1; 435/325; 536/23.5

[58] Field of Search .............................. 435/69.1, 6, 7.1, 435/320.1, 240.2; 536/23.1, 23.5

[56] References Cited

U.S. PATENT DOCUMENTS 5,128,254  7/1992  Sibley et al. ..................... 435/172.3

OTHER PUBLICATIONS

Masu et al. "cDNA Cloning of Bovine Substance-K Receptor Through Oocyte Expression System", Nature, vol. 328, 29 Oct. 1987, pp. 836–838.

Kaufman, "Vectors Used for Expression in Mammalian Cells", Methods in Enzymology, vol. 185, 1990, pp. 487–511.

Scarborough et al., "Tethered Ligand Agonist Peptides", *The Journal of Biological Chemistry* 267(19):13146–49 (1992).

*Primary Examiner*—David Guzo
*Attorney, Agent, or Firm*—Morrison & Foerster LLP

[57] ABSTRACT

The DNA encoding the C140 cell surface receptor has been cloned and sequenced. The availability of this DNA permits the recombinant production of the C140 receptor which can be produced at cell or oocyte surfaces and is useful in assay systems both for the detection of substances which affect its activity, including agonists and antagonists. Further, the elucidation of the structure of the C140 receptor permits the design of agonist and antagonist compounds which are useful in these assays. The availability of the C140 receptor also permits production of antibodies specifically immunoreactive with the receptor per se or with specific regions thereof.

7 Claims, 11 Drawing Sheets

```
                CCCTGTCAGTCTTAAGATTCTAGAAGTCGCTGTCCTATACGGAACCCAAAA
     CTCTCACTGTTAATGAAATACCATTGTCGGGGCGAAGATGTAGCTCAGTGGTAAAATACT -121
     TGCCAGCACACACAAGAATTAGACTTCAACCGTCACCAACTGCCCTGTGTAGGACGGTCG
     GTCACTGAAAGAGAATATTGTCTGCAATACTCTAATGACATCTGTCTGTGTTCATCTGAA -1
    ─────────────────────────────────────SP──────────────────────
   1 MetPheHisLeuLysHisSerSerLeuThrValGlyProPheIleSerValMetIleLeu
     ATGTTCCATTTAAAACACAGCAGCCTTACTGTTGGACCATTTATCTCAGTAATGATTCTG
    ─────────────────────────▼─────────────▽─────────────────────
     LeuArgPheLeuCysThrGlyArgAsnAsnSerLysGlyArgSerLeuIleGlyArgLeu
     CTCCGCTTTCTTTGTACAGGACGCAACAACAGTAAAGGAAGAAGTCTTATTGGCAGATTA 120

41 GluThrGlnProProIleThrGlyLysGlyValProValGluProGlyPheSerIleAsp
     GAAACCCAGCCTCCAATCACTGGGAAAGGGGTTCCGGTAGAACCAGGCTTTTCCATCGAT

──────────────
     GluPheSerAlaSerIleLeuThrGlyLysLeuThrThrValPheLeuProValValTyr
     GAGTTCTCTGCGTCCATCCTCACCGGGAAGCTGACCACGGTCTTTCTTCCGGTCGTCTAC 240
    ─────────────────────────I───────────────────────────────────
  81 IleIleValPheValIleGlyLeuProSerAsnGlyMetAlaLeuTrpIlePheLeuPhe
     ATTATTGTGTTTGTGATTGGTTTGCCCAGTAATGGCATGGCCCTCTGGATCTTCCTTTTC
                                 ────────────────II────────────────
     ArgThrLysLysLysHisProAlaValIleTyrMetAlaAsnLeuAlaLeuAlaAspLeu
     CGAACGAAGAAGAAACACCCCGCCGTGATTTACATGGCCAACCTGGCCTTGGCCGACCTC 360

121 LeuSerValIleTrpPheProLeuLysIleSerTyrHisLeuHisGlyAsnAsnTrpVal
     CTCTCTGTCATCTGGTTCCCCCTGAAGATCTCCTACCACCTACATGGCAACAACTGGGTC
                                  ──────────III──────────────────
     TyrGlyGluAlaLeuCysLysValLeuIleGlyPhePheTyrGlyAsnMetTyrCysSer
     TACGGGGAGGCCCTGTGCAAGGTGCTCATTGGCTTTTTCTATGGTAACATGTATTGCTCC 480

161 IleLeuPheMetThrCysLeuSerValGlnArgTyrTrpValIleValAsnProMetGly
     ATCCTCTTCATGACCTGCCTCAGCGTGCAGAGGTACTGGGTGATCGTGAACCCCATGGGA
                                    ──────────IV─────────────────
     HisProArgLysLysAlaAsnIleAlaValGlyValSerLeuAlaIleTrpLeuLeuIle
     CACCCCAGGAAGAAGGCAAACATCGCCGTTGGCGTCTCCTTGGCAATCTGGCTCCTGATT 600
```

FIG.IA

```
201 PheLeuValThrIleProLeuTyrValMetLysGlnThrIleTyrIleProAlaLeuAsn
    TTTCTGGTCACCATCCCTTTGTATGTCATGAAGCAGACCATCTACATTCCAGCATTGAAC

IleThrThrCysHisAspValLeuProGluGluValLeuValGlyAsnMetPheAsnTyr
    ATCACCACCTGTCACGATGTGCTGCCTGAGGAGGTATTGGTGGGGGACATGTTCAATTAC 720
                                              ─── V ───
241 PheLeuSerLeuAlaIleGlyValPheLeuPheProAlaLeuLeuThrAlaSerAlaTyr
    TTCCTCTCACTGGCCATTGGAGTCTTCCTGTTCCCGGCCCTCCTTACTGCATCTGCCTAC

ValLeuMetIleLysThrLeuArgSerSerAlaMetAspGluHisSerGluLysLysArg
    GTGCTCATGATCAAGACGCTCCGCTCTTCTGCTATGGATGAACACTCAGAGAACAAAAGG 840
                                        ─── VI ───
281 GlnArgAlaIleArgLeuIleIleThrValLeuAlaMetTyrPheIleCysPheAlaPro
    CAGAGGGCTATCCGACTCATCATCACCGTGCTGGCCATGTACTTCATCTGCTTTCGTCCT

SerAsnLeuLeuLeuValValHisTyrPheLeuIleLysThrGlnArgGlnSerHisVal
    AGCAACCTTCTGCTCGTAGTGCATTATTTCCTAATCAAAACCCAGAGGCAGAGCCACGTC 960
                                          ─── VII ───
321 TyrAlaLeuTyrLeuValAlaLeuCysLeuSerThrLeuAsnSerCysIleAspProPhe
    TACGCCCTCTACCTTGTCGCCCTCTGCCTGTCGACCCTCAACAGCTGCATAGACCCCTTT

ValTyrTyrPheValSerLysAspPheArgAspHisAlaArgAsnAlaLeuLeuCysArg
    GTCTATTACTTTGTCTCAAAAGATTTCAGGGATCACGCCAGAAACGCGCTCCTCTGCCGA 1080

361 SerValArgThrValAsnArgMetGlnIleSerLeuSerSerAsnLysPheSerArgLys
    AGTGTCCGCACTGTGAATCGCATGCAAATCTCGCTCAGCTCCAACAAGTTCTCCAGGAAG
    GATGTCAAGCCTGCTTGATGATGATGATGATGATGGTGTGTGTGTG              1246

SerGlySerTyrSerSerSerSerThrSerValLysThrSerTyr
    TCCGGCTCCTACTCTTCAAGCTCAACCAGTGTTAAAACCTCCTACTGAGCTGTACCTGAG 1200
```

FIG. IB

```
CGCTCCAGGCCTGGGTGACAGCGAGACCCTGTCTCATAAATTAAAAAATGAATAA
                                           ─── SP ──────────────
MetAsnValLeuSerPheGluGlnThrSerValThrAlaGluThrPheIleSerValMet
ATGAATGTACTTTCATTTGAACAAACCAGTGTTACTGCTGAAACATTTATTTCTGTAATG
                          ▼                    ▽
ThrLeuValPheLeuSerCysThrGlyThrAsnArgSerSerLysGlyArgSerLeuIle    -1
ACCCTTGTCTTCCTTTCTTGTACAGGAACCAATAGATCCTCTAAAGGAAGAAGCCTTATT  120

GlyLysValAspGlyThrSerHisValThrGlyLysGlyValThrValGluThrValPhe
GGTAAGGTTGATGGCACATCCCACGTCACTGGAAAAGGAGTTACAGTTGAAACAGTCTTT

SerValAspGluPheSerAlaSerValLeuThrGlyLysLeuThrThrValPheLeuPro
TCTGTGGATGAGTTTTCTGCATCTGTCCTCACTGGAAAACTGACCACTGTCTTCCTTCCA  240
                                        ─── I ──────────
IleValTyrThrIleValPheValValGlyLeuProSerAsnGlyMetAlaLeuTrpVal
ATTGTCTACACAATTGTGTTTGTGGTGGGTTTGCCAAGTAACGGCATGGCCCTGTGGGTC

PheLeuPheArgThrLysLysLysHisProAlaValIleTyrMetAlaAsnLeuAlaLeu
TTTCTTTTCCGAACTAAGAAGAAGCACCCTGCTGTGATTTACATGGCCAATCTGGCCTTG  360
    ── II ─────────────
AlaAspLeuLeuSerValIleTrpPheProLeuLysIleAlaTyrHisIleHisGlyAsn
GCTGACCTCCTCTCTGTCATCTGGTTCCCCCTTGAAGATTGCCTATCACATACATGGCAAC

AsnTrpIleTyrGlyGluAlaLeuCysAsnValLeuIleGlyPhePheTyrGlyAsnMet
AACTGGATTTATGGGGAAGCTCTTTGTAATGTGCTTATTGGCTTTTTCTATGGCAACATG  480
    ── III ──────────
TyrCysSerIleLeuPheMetThrCysLeuSerValGlnArgTyrTrpValIleValAsn
TACTGTTCCATTCTCTTCATGACCTGCCTCAGTGTGCAGAGGTATTGGGTCATCGTGAAC

ProMetGlyHisSerArgLysLysAlaAsnIleAlaIleGlyIleSerLeuAlaIleTrp
CCCATGGGGCACTCCAGGAAGAAGGCAAACATTGCCATTGGCATCTCCCTGGCAATATGG  600
```

FIG. 2A

```
                  IV
LeuLeuIleLeuLeuValThrIleProLeuTyrValValLysGlnThrIlePheIlePro
CTGCTGATTCTGCTGGTCACCATCCCTTTGTATGTCGTGAAGCAGACCATCTTCATTCCT
        ▼
AlaLeuAsnIleThrThrCysHisAspValLeuProGluGlnLeuLeuValGlyAspMet
GCCCTGAACATCACGACCTGTCATGATGTTTTGCCTGAGCAGCTCTTGGTGGGAGACATG   720

V
PheAsnTyrPheLeuSerLeuAlaIleGlyValPheLeuPheProAlaPheLeuThrAla
TTCAATTACTTCCTCTCTCTGGCCATTGGGGTCTTTCTGTTCCCAGCCTTCCTCACAGCC

SerAlaTyrValLeuMetIleArgMetLeuArgSerSerAlaMetAspGluAsnSerGlu
TCTGCCTATGTGCTGATGATCAGAATGCTGCGATCTTCTGCCATGGATGAAAACTCAGAG   840

VI
LysLysArgLysArgAlaIleLysLeuIleValThrValLeuAlaMetTyrLeuIleCys
AAGAAAAGGAAGAGGGCCATCAAACTCATTGTCACTGTCCTGGCCATGTACCTGATCTGC

PheThrProSerAsnLeuLeuLeuValValHisTyrPheLeuIleLysSerGlnGlyGln
TTCACTCCTAGTAACCTTCTGCTTGTGGTGCATTATTTTCTGATTAAGAGCCAGGGCCAG   960

VII
SerHisValTyrAlaLeuTyrIleValAlaLeuCysLeuSerThrLeuAsnSerCysIle
AGCCATGTCTATGCCCTGTACATTGTAGCCCTCTGCCTCTCTACCCTTAACAGCTGCATC

AspProPheValTyrTyrPheValSerHisAspPheArgAspHisAlaLysAsnAlaLeu
GACCCCTTTGTCTATTACTTTGTTTCACATGATTTCAGGGATCATGCAAAGAACGCTCTC   1080

LeuCysArgSerValArgThrValLysGlnMetGlnValSerLeuThrSerLysLysHis
CTTTGCCGAAGTGTCCGCACTGTAAAGCAGATGCAAGTATCCCTCACCTCAAAGAAACAC

SerArgLysSerSerSerTyrSerSerSerSerThrThrValLysThrSerTyr *
TCCAGGAAATCCAGCTCTTACTCTTCAAGTTCAACCACTGTTAAGACCTCCTATTGAGTT   1200
```

F I G. 2 B

```
Mouse C140  M--FHLKHSS LIVGPFISVM ILLRFLCTGR NNSHKGRSLI GRLETQPPIT   47
Human C140  MNVLSFEQTS VIAETFISVM ILVFLSCTGT NRSSKGRSLI GKVDGTSHVI   50

Mouse C140  GKGVFVEPGF SIDEFSASIL TCKLTTVFLP VVYIIVFVIG LPSNGMALWI   97
Human C140  GKGVIVEIVF SMDEFSASML TGKLTTVFLP IVYIIVFVVG LPSNGMALWV  100

Mouse C140  FLFRTKKKHP AVIYMANLAL ADLLSVIWFP LKISYHLHGN NWMYGEALCK  147
Human C140  FLFRTKKKHP AVIYMANLAL ADLLSVIWFP LKIAYHIHGN NWIYGEALCN  150

Mouse C140  VLIGFFYGNM YCSILFMTCL SVQRYWVIVN PMGHPRKKAN IAMGVSLAIW  197
Human C140  VLIGFFYGNM YCSILFMTCL SVQRYWVIVN PMGHSRKKAN IAIGISLAIW  200

Mouse C140  LLIFLVTIPL YVMKQTIYIP ALNITTCHDV LPEEVLVGDM FNYFLSLAIG  247
Human C140  LLILLVTIPL YVMKQTIPIP ALNITTCHDV LPEQLLVGDM FNYFLSLAIG  250

Mouse C140  VFLFPALLTA SAYVLMIKTL RSSAMDEHSE KKRQRAIRLI IITVLAMYFIC  297
Human C140  VFLFPAFLTA SAYVLMIRML RSSAMDENSE KKRKRAIKLI MTVLAMYLIC  300

Mouse C140  FAPSNLLLVV HYFLIKIQRQ SHVYALYLVA LCLSTLNSCI DPFVYYFVSK  347
Human C140  FIPSNLLLVV HYFLIKSQGQ SHVYALYIVA LCLSTLNSCI DPFVYYFVSH  350

Mouse C140  DFRDHARNAL LCRSVRTVNR MQISLSSNKF SRKSGSYSSS STSVKTSY    395
Human C140  DFRDHAKNAL LCRSVRTVKQ MQVSLISKKH SRKSSSYSSS STTVKTSY    398
```

FIG.3

```
C140    MFHLKHSSLTVGPFISVMILLRFLCTGRNNSK------GRSLIGRLETQP----                         44
        SP                                          ▼
HSTHRR  MGPRRLLLVAACFSLCGPLLSARTRARRPESKATNATLDPRSFLLRNPNDKYEPEWEDEE                  60
                                                                  I
C140    --------PITGKGVPVEPGFSIDEFSASILTGKLTTVFLPVVYIIVFIGLPSN                         91
HSTHRR  KNESGLTEYRLVSINKSSPLQKQLPAFISEDASGYLTSSWLTLFVPSVYTGVFVVSLPLN                  120
                                                        II
C140    GMALWIEFLFRTKKKHPAVIYMANLALADLLSVIWFPLKISYHLHGNNWVYGEALCKVLIG                  151
HSTHRR  IMAIVVFILKMKVKKPAVVYMLHLATADVLFVSVLPFKISYYFSGSDWQFGSELCRFVTA                  180
                                                                 IV
C140    FFYGNMYCSILFMTCLSVQRYWVIVNPM-GHPRKKANIAVGVSLAIWLLIFLVTIPLYVM                   210
HSTHRR  AFYCNMYASILLMTVISIDRFLAVVYPMQSLSWRTLGRASFTCLAIWALAIAGVVPLVLK                   240
                                                      V
C140    KQTIYIPALNITTCHDVLPEEVLVGDMFNYFLSLAIGVFLFPALLTASAYVLMIKTLRSS                   270
HSTHRR  EQTIQVPGLNITTCHDVLNETLLEGYYAYFSAFSAVFFFVPLIISTVCVVSIIRCLSSS                    300
C140    AMDEHSEKKRQRAIRLIITVLAMYFICFAPSNLLLVVHY-FLIKTQRQSHVVALYLVALC                   329
HSTHRR  AVANRSKKKSR--ALFLSAAVFCIFIICFGPTNVLIAHYSFLSHTSTTEAAYFAYLLCVC                   358
                                                     VII
C140    LSTLNSCIDPFVYYFVSKDFRDHARNALLCRSVRTVNRMQISLSSNKFSRKSGSYSSSST                   389
HSTHRR  VSSISSCIDPLIYYYASSECQRYVYSILCCKESSDPSSYNSSGQLMASKMDTCSSNLNNS                   418
C140    SVKTSY-                                                                       395
HSTHRR  IYKKLLT                                                                       426
```

FIG. 5

SEQUENCE LISTING ( 1 ) GENERAL INFORMATION:

( i i i ) NUMBER OF SEQUENCES: 59

( 2 ) INFORMATION FOR SEQ ID NO:1:

( i ) SEQUENCE CHARACTERISTICS:
      ( A ) LENGTH: 1475 base pairs
      ( B ) TYPE: nucleic acid
      ( C ) STRANDEDNESS: single
      ( D ) TOPOLOGY: linear ( i x ) FEATURE:
      ( A ) NAME/KEY: CDS
      ( B ) LOCATION: 232..1416

( i x ) FEATURE:
      ( A ) NAME/KEY: mat_peptide
      ( B ) LOCATION: 232

( x i ) SEQUENCE DESCRIPTION: SEQ ID NO:1:

```
CCCTGTCAGT CTTAAGATTC TAGAAGTCGC TGTCCTATAC GGAACCCAAA ACTCTCACTG         60

TTAATGAAAT ACCATTGTCG GGGCGAAGAT GTAGCTCAGT GGTAAAATAC TTGCCAGCAC        120

ACACAAGAAT TAGACTTCAA CCGTCACCAA CTGCCCTGTG TAGGACGGTC GGTCACTGAA        180

AGAGAATATT GTCTGCAATA CTCTAATGAC ATCTGTCTGT GTTCATCTGA A ATG TTC        237
                                                         Met Phe
                                                           1

CAT TTA AAA CAC AGC AGC CTT ACT GTT GGA CCA TTT ATC TCA GTA ATG          285
His Leu Lys His Ser Ser Leu Thr Val Gly Pro Phe Ile Ser Val Met
        5               10                  15

ATT CTG CTC CGC TTT CTT TGT ACA GGA CGC AAC AAC AGT AAA GGA AGA          333
Ile Leu Leu Arg Phe Leu Cys Thr Gly Arg Asn Asn Ser Lys Gly Arg
        20              25                  30

AGT CTT ATT GGC AGA TTA GAA ACC CAG CCT CCA ATC ACT GGG AAA GGG          381
Ser Leu Ile Gly Arg Leu Glu Thr Gln Pro Pro Ile Thr Gly Lys Gly
35              40                  45                      50

GTT CCG GTA GAA CCA GGC TTT TCC ATC GAT GAG TTC TCT GCG TCC ATC          429
Val Pro Val Glu Pro Gly Phe Ser Ile Asp Glu Phe Ser Ala Ser Ile
                55                  60                  65

CTC ACC GGG AAG CTG ACC ACG GTC TTT CTT CCG GTC GTC TAC ATT ATT          477
Leu Thr Gly Lys Leu Thr Thr Val Phe Leu Pro Val Val Tyr Ile Ile
            70                  75                  80

GTG TTT GTG ATT GGT TTG CCC AGT AAT GGC ATG GCC CTC TGG ATC TTC          525
Val Phe Val Ile Gly Leu Pro Ser Asn Gly Met Ala Leu Trp Ile Phe
        85                  90                  95

CTT TTC CGA ACG AAG AAG AAA CAC CCC GCC GTG ATT TAC ATG GCC AAC          573
Leu Phe Arg Thr Lys Lys Lys His Pro Ala Val Ile Tyr Met Ala Asn
    100                 105                 110

CTG GCC TTG GCC GAC CTC CTC TCT GTC ATC TGG TTC CCC CTG AAG ATC          621
Leu Ala Leu Ala Asp Leu Leu Ser Val Ile Trp Phe Pro Leu Lys Ile
115                 120                 125                 130

TCC TAC CAC CTA CAT GGC AAC AAC TGG GTC TAC GGG GAG GCC CTG TGC          669
Ser Tyr His Leu His Gly Asn Asn Trp Val Tyr Gly Glu Ala Leu Cys
                135                 140                 145

AAG GTG CTC ATT GGC TTT TTC TAT GGT AAC ATG TAT TGC TCC ATC CTC          717
Lys Val Leu Ile Gly Phe Phe Tyr Gly Asn Met Tyr Cys Ser Ile Leu
            150                 155                 160

TTC ATG ACC TGC CTC AGC GTG CAG AGG TAC TGG GTG ATC GTG AAC CCC          765
Phe Met Thr Cys Leu Ser Val Gln Arg Tyr Trp Val Ile Val Asn Pro
        165                 170                 175

ATG GGA CAC CCC AGG AAG AAG GCA AAC ATC GCC GTT GGC GTC TCC TTG          813
Met Gly His Pro Arg Lys Lys Ala Asn Ile Ala Val Gly Val Ser Leu
    180                 185                 190

GCA ATC TGG CTC CTG ATT TTT CTG GTC ACC ATC CCT TTG TAT GTC ATG          861
Ala Ile Trp Leu Leu Ile Phe Leu Val Thr Ile Pro Leu Tyr Val Met
195                 200                 205                 210

AAG CAG ACC ATC TAC ATT CCA GCA TTG AAC ATC ACC ACC TGT CAC GAT          909
Lys Gln Thr Ile Tyr Ile Pro Ala Leu Asn Ile Thr Thr Cys His Asp
                215                 220                 225

GTG CTG CCT GAG GAG GTA TTG GTG GGG GAC ATG TTC AAT TAC TTC CTC          957
Val Leu Pro Glu Glu Val Leu Val Gly Asp Met Phe Asn Tyr Phe Leu
            230                 235                 240

TCA CTG GCC ATT GGA GTC TTC CTG TTC CCG GCC CTC CTT ACT GCA TCT         1005
Ser Leu Ala Ile Gly Val Phe Leu Phe Pro Ala Leu Leu Thr Ala Ser
        245                 250                 255

GCC TAC GTG CTC ATG ATC AAG ACG CTC CGC TCT TCT GCT ATG GAT GAA         1053
Ala Tyr Val Leu Met Ile Lys Thr Leu Arg Ser Ser Ala Met Asp Glu
    260                 265                 270
```

| | | | | | | | | | | | | | | | | |
|---|---|---|---|---|---|---|---|---|---|---|---|---|---|---|---|---|
| CAC | TCA | GAG | AAC | AAA | AGG | CAG | AGG | GCT | ATC | CGA | CTC | ATC | ATC | ACC | GTG | 1101 |
| His | Ser | Glu | Asn | Lys | Arg | Gln | Arg | Ala | Ile | Arg | Leu | Ile | Ile | Thr | Val | |
| 275 | | | | 280 | | | | | 285 | | | | | | 290 | |
| CTG | GCC | ATG | TAC | TTC | ATC | TGC | TTT | GCT | CCT | AGC | AAC | CTT | CTG | CTC | GTA | 1149 |
| Leu | Ala | Met | Tyr | Phe | Ile | Cys | Phe | Ala | Pro | Ser | Asn | Leu | Leu | Leu | Val | |
| | | | | 295 | | | | | 300 | | | | | 305 | | |
| GTG | CAT | TAT | TTC | CTA | ATC | AAA | ACC | CAG | AGG | CAG | AGC | CAC | GTC | TAC | GCC | 1197 |
| Val | His | Tyr | Phe | Leu | Ile | Lys | Thr | Gln | Arg | Gln | Ser | His | Val | Tyr | Ala | |
| | | | 310 | | | | | 315 | | | | | 320 | | | |
| CTC | TAC | CTT | GTC | GCC | CTC | TGC | CTG | TCG | ACC | CTC | AAC | AGC | TGC | ATA | GAC | 1245 |
| Leu | Tyr | Leu | Val | Ala | Leu | Cys | Leu | Ser | Thr | Leu | Asn | Ser | Cys | Ile | Asp | |
| | | 325 | | | | | 330 | | | | | 335 | | | | |
| CCC | TTT | GTC | TAT | TAC | TTT | GTC | TCA | AAA | GAT | TTC | AGG | GAT | CAC | GCC | AGA | 1293 |
| Pro | Phe | Val | Tyr | Tyr | Phe | Val | Ser | Lys | Asp | Phe | Arg | Asp | His | Ala | Arg | |
| | 340 | | | | | 345 | | | | | 350 | | | | | |
| AAC | GCG | CTC | CTC | TGC | CGA | AGT | GTC | CGC | ACT | GTG | AAT | CGC | ATG | CAA | ATC | 1341 |
| Asn | Ala | Leu | Leu | Cys | Arg | Ser | Val | Arg | Thr | Val | Asn | Arg | Met | Gln | Ile | |
| 355 | | | | | 360 | | | | | 365 | | | | | 370 | |
| TCG | CTC | AGC | TCC | AAC | AAG | TTC | TCC | AGG | AAG | TCC | GGC | TCC | TAC | TCT | TCA | 1389 |
| Ser | Leu | Ser | Ser | Asn | Lys | Phe | Ser | Arg | Lys | Ser | Gly | Ser | Tyr | Ser | Ser | |
| | | | | 375 | | | | | 380 | | | | | 385 | | |
| AGC | TCA | ACC | AGT | GTT | AAA | ACC | TCC | TAC | TGAGCTGTAC | | CTGAGGATGT | | | | | 1436 |
| Ser | Ser | Thr | Ser | Val | Lys | Thr | Ser | Tyr | | | | | | | | |
| | | | 390 | | | | | 395 | | | | | | | | |

CAAGCCTGCT TGATGATGAT GATGATGATG GTGTGTGTG                                    1475

( 2 ) INFORMATION FOR SEQ ID NO:2:

( i ) SEQUENCE CHARACTERISTICS:
        ( A ) LENGTH: 395 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Phe | His | Leu | Lys | His | Ser | Ser | Leu | Thr | Val | Gly | Pro | Phe | Ile | Ser |
| 1 | | | | 5 | | | | | 10 | | | | | 15 | |
| Val | Met | Ile | Leu | Leu | Arg | Phe | Leu | Cys | Thr | Gly | Arg | Asn | Asn | Ser | Lys |
| | | | 20 | | | | | 25 | | | | | 30 | | |
| Gly | Arg | Ser | Leu | Ile | Gly | Arg | Leu | Glu | Thr | Gln | Pro | Pro | Ile | Thr | Gly |
| | | 35 | | | | | 40 | | | | | 45 | | | |
| Lys | Gly | Val | Pro | Val | Glu | Pro | Gly | Phe | Ser | Ile | Asp | Glu | Phe | Ser | Ala |
| | 50 | | | | | 55 | | | | | 60 | | | | |
| Ser | Ile | Leu | Thr | Gly | Lys | Leu | Thr | Thr | Val | Phe | Leu | Pro | Val | Val | Tyr |
| 65 | | | | | 70 | | | | | 75 | | | | | 80 |
| Ile | Ile | Val | Phe | Val | Ile | Gly | Leu | Pro | Ser | Asn | Gly | Met | Ala | Leu | Trp |
| | | | | 85 | | | | | 90 | | | | | 95 | |
| Ile | Phe | Leu | Phe | Arg | Thr | Lys | Lys | Lys | His | Pro | Ala | Val | Ile | Tyr | Met |
| | | | 100 | | | | | 105 | | | | | 110 | | |
| Ala | Asn | Leu | Ala | Leu | Ala | Asp | Leu | Leu | Ser | Val | Ile | Trp | Phe | Pro | Leu |
| | | 115 | | | | | 120 | | | | | 125 | | | |
| Lys | Ile | Ser | Tyr | His | Leu | His | Gly | Asn | Asn | Trp | Val | Tyr | Gly | Glu | Ala |
| | 130 | | | | | 135 | | | | | 140 | | | | |
| Leu | Cys | Lys | Val | Leu | Ile | Gly | Phe | Phe | Tyr | Gly | Asn | Met | Tyr | Cys | Ser |
| 145 | | | | | 150 | | | | | 155 | | | | | 160 |
| Ile | Leu | Phe | Met | Thr | Cys | Leu | Ser | Val | Gln | Arg | Tyr | Trp | Val | Ile | Val |
| | | | | 165 | | | | | 170 | | | | | 175 | |

|  |  |  |  |  |  |  |  |  |  |  |  |  |  |  |
|---|---|---|---|---|---|---|---|---|---|---|---|---|---|---|
| Asn | Pro | Met | Gly<br>180 | His | Pro | Arg | Lys | Lys<br>185 | Ala | Asn | Ile | Ala | Val<br>190 | Gly | Val |
| Ser | Leu | Ala<br>195 | Ile | Trp | Leu | Leu | Ile<br>200 | Phe | Leu | Val | Thr | Ile<br>205 | Pro | Leu | Tyr |
| Val | Met<br>210 | Lys | Gln | Thr | Ile | Tyr<br>215 | Ile | Pro | Ala | Leu | Asn<br>220 | Ile | Thr | Thr | Cys |
| His<br>225 | Asp | Val | Leu | Pro | Glu<br>230 | Glu | Val | Leu | Val | Gly<br>235 | Asp | Met | Phe | Asn | Tyr<br>240 |
| Phe | Leu | Ser | Leu | Ala<br>245 | Ile | Gly | Val | Phe | Leu<br>250 | Phe | Pro | Ala | Leu | Leu<br>255 | Thr |
| Ala | Ser | Ala | Tyr<br>260 | Val | Leu | Met | Ile | Lys<br>265 | Thr | Leu | Arg | Ser | Ser<br>270 | Ala | Met |
| Asp | Glu | His<br>275 | Ser | Glu | Asn | Lys | Arg<br>280 | Gln | Arg | Ala | Ile | Arg<br>285 | Leu | Ile | Ile |
| Thr | Val<br>290 | Leu | Ala | Met | Tyr | Phe<br>295 | Ile | Cys | Phe | Ala | Pro<br>300 | Ser | Asn | Leu | Leu |
| Leu<br>305 | Val | Val | His | Tyr | Phe<br>310 | Leu | Ile | Lys | Thr | Gln<br>315 | Arg | Gln | Ser | His | Val<br>320 |
| Tyr | Ala | Leu | Tyr | Leu<br>325 | Val | Ala | Leu | Cys | Leu<br>330 | Ser | Thr | Leu | Asn | Ser<br>335 | Cys |
| Ile | Asp | Pro | Phe<br>340 | Val | Tyr | Tyr | Phe | Val<br>345 | Ser | Lys | Asp | Phe | Arg<br>350 | Asp | His |
| Ala | Arg | Asn<br>355 | Ala | Leu | Leu | Cys | Arg<br>360 | Ser | Val | Arg | Thr | Val<br>365 | Asn | Arg | Met |
| Gln | Ile<br>370 | Ser | Leu | Ser | Ser | Asn<br>375 | Lys | Phe | Ser | Arg | Lys<br>380 | Ser | Gly | Ser | Tyr |
| Ser<br>385 | Ser | Ser | Ser | Thr | Ser<br>390 | Val | Lys | Thr | Ser | Tyr<br>395 |  |  |  |  |  |

( 2 ) INFORMATION FOR SEQ ID NO:3:

( i ) SEQUENCE CHARACTERISTICS:
        ( A ) LENGTH: 1255 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 56..1249

( i x ) FEATURE:
        ( A ) NAME/KEY: mat_peptide
        ( B ) LOCATION: 56

( x i ) SEQUENCE DESCRIPTION: SEQ ID NO:3:

| CGCTCCAGGC | CTGGGTGACA | GCGAGACCCT | GTCTCATAAA | TTAAAAAATG | AATAA | ATG<br>Met<br>1 | 58 |
|---|---|---|---|---|---|---|---|

| AAT<br>Asn | GTA<br>Val | CTT<br>Leu | TCA<br>Ser<br>5 | TTT<br>Phe | GAA<br>Glu | CAA<br>Gln | ACC<br>Thr | AGT<br>Ser<br>10 | GTT<br>Val | ACT<br>Thr | GCT<br>Ala | GAA<br>Glu | ACA<br>Thr<br>15 | TTT<br>Phe | ATT<br>Ile | 106 |
|---|---|---|---|---|---|---|---|---|---|---|---|---|---|---|---|---|
| TCT<br>Ser | GTA<br>Val | ATG<br>Met<br>20 | ACC<br>Thr | CTT<br>Leu | GTC<br>Val | TTC<br>Phe | CTT<br>Leu<br>25 | TCT<br>Ser | TGT<br>Cys | ACA<br>Thr | GGA<br>Gly | ACC<br>Thr<br>30 | AAT<br>Asn | AGA<br>Arg | TCC<br>Ser | 154 |
| TCT<br>Ser | AAA<br>Lys<br>35 | GGA<br>Gly | AGA<br>Arg | AGC<br>Ser | CTT<br>Leu | ATT<br>Ile<br>40 | GGT<br>Gly | AAG<br>Lys | GTT<br>Val | GAT<br>Asp | GGC<br>Gly<br>45 | ACA<br>Thr | TCC<br>Ser | CAC<br>His | GTC<br>Val | 202 |
| ACT<br>Thr<br>50 | GGA<br>Gly | AAA<br>Lys | GGA<br>Gly | GTT<br>Val | ACA<br>Thr<br>55 | GTT<br>Val | GAA<br>Glu | ACA<br>Thr | GTC<br>Val | TTT<br>Phe<br>60 | TCT<br>Ser | GTG<br>Val | GAT<br>Asp | GAG<br>Glu | TTT<br>Phe<br>65 | 250 |

| | | | | | | | | | | | | | | | | |
|---|---|---|---|---|---|---|---|---|---|---|---|---|---|---|---|---|
| TCT | GCA | TCT | GTC | CTC | ACT | GGA | AAA | CTG | ACC | ACT | GTC | TTC | CTT | CCA | ATT | 298 |
| Ser | Ala | Ser | Val | Leu | Thr | Gly | Lys | Leu | Thr | Thr | Val | Phe | Leu | Pro | Ile | |
| | | | | 70 | | | | | 75 | | | | | | 80 | |
| GTC | TAC | ACA | ATT | GTG | TTT | GTG | GTG | GGT | TTG | CCA | AGT | AAC | GGC | ATG | GCC | 346 |
| Val | Tyr | Thr | Ile | Val | Phe | Val | Val | Gly | Leu | Pro | Ser | Asn | Gly | Met | Ala | |
| | | | 85 | | | | | 90 | | | | | 95 | | | |
| CTG | TGG | GTC | TTT | CTT | TTC | CGA | ACT | AAG | AAG | AAG | CAC | CCT | GCT | GTG | ATT | 394 |
| Leu | Trp | Val | Phe | Leu | Phe | Arg | Thr | Lys | Lys | Lys | His | Pro | Ala | Val | Ile | |
| | | 100 | | | | | | 105 | | | | | 110 | | | |
| TAC | ATG | GCC | AAT | CTG | GCC | TTG | GCT | GAC | CTC | CTC | TCT | GTC | ATC | TGG | TTC | 442 |
| Tyr | Met | Ala | Asn | Leu | Ala | Leu | Ala | Asp | Leu | Leu | Ser | Val | Ile | Trp | Phe | |
| | 115 | | | | | 120 | | | | | 125 | | | | | |
| CCC | TTG | AAG | ATT | GCC | TAT | CAC | ATA | CAT | GGC | AAC | AAC | TGG | ATT | TAT | GGG | 490 |
| Pro | Leu | Lys | Ile | Ala | Tyr | His | Ile | His | Gly | Asn | Asn | Trp | Ile | Tyr | Gly | |
| 130 | | | | | 135 | | | | 140 | | | | | | 145 | |
| GAA | GCT | CTT | TGT | AAT | GTG | CTT | ATT | GGC | TTT | TTC | TAT | GGC | AAC | ATG | TAC | 538 |
| Glu | Ala | Leu | Cys | Asn | Val | Leu | Ile | Gly | Phe | Phe | Tyr | Gly | Asn | Met | Tyr | |
| | | | | 150 | | | | | 155 | | | | | 160 | | |
| TGT | TCC | ATT | CTC | TTC | ATG | ACC | TGC | CTC | AGT | GTG | CAG | AGG | TAT | TGG | GTC | 586 |
| Cys | Ser | Ile | Leu | Phe | Met | Thr | Cys | Leu | Ser | Val | Gln | Arg | Tyr | Trp | Val | |
| | | | 165 | | | | | 170 | | | | | 175 | | | |
| ATC | GTG | AAC | CCC | ATG | GGG | CAC | TCC | AGG | AAG | AAG | GCA | AAC | ATT | GCC | ATT | 634 |
| Ile | Val | Asn | Pro | Met | Gly | His | Ser | Arg | Lys | Lys | Ala | Asn | Ile | Ala | Ile | |
| | | 180 | | | | | 185 | | | | | 190 | | | | |
| GGC | ATC | TCC | CTG | GCA | ATA | TGG | CTG | CTG | ATT | CTG | CTG | GTC | ACC | ATC | CCT | 682 |
| Gly | Ile | Ser | Leu | Ala | Ile | Trp | Leu | Leu | Ile | Leu | Leu | Val | Thr | Ile | Pro | |
| | 195 | | | | | 200 | | | | | 205 | | | | | |
| TTG | TAT | GTC | GTG | AAG | CAG | ACC | ATC | TTC | ATT | CCT | GCC | CTG | AAC | ATC | ACG | 730 |
| Leu | Tyr | Val | Val | Lys | Gln | Thr | Ile | Phe | Ile | Pro | Ala | Leu | Asn | Ile | Thr | |
| 210 | | | | | 215 | | | | | 220 | | | | | 225 | |
| ACC | TGT | CAT | GAT | GTT | TTG | CCT | GAG | CAG | CTC | TTG | GTG | GGA | GAC | ATG | TTC | 778 |
| Thr | Cys | His | Asp | Val | Leu | Pro | Glu | Gln | Leu | Leu | Val | Gly | Asp | Met | Phe | |
| | | | | 230 | | | | | 235 | | | | | 240 | | |
| AAT | TAC | TTC | CTC | TCT | CTG | GCC | ATT | GGG | GTC | TTT | CTG | TTC | CCA | GCC | TTC | 826 |
| Asn | Tyr | Phe | Leu | Ser | Leu | Ala | Ile | Gly | Val | Phe | Leu | Phe | Pro | Ala | Phe | |
| | | | 245 | | | | | 250 | | | | | 255 | | | |
| CTC | ACA | GCC | TCT | GCC | TAT | GTG | CTG | ATG | ATC | AGA | ATG | CTG | CGA | TCT | TCT | 874 |
| Leu | Thr | Ala | Ser | Ala | Tyr | Val | Leu | Met | Ile | Arg | Met | Leu | Arg | Ser | Ser | |
| | | 260 | | | | | 265 | | | | | 270 | | | | |
| GCC | ATG | GAT | GAA | AAC | TCA | GAG | AAG | AAA | AGG | AAG | AGG | GCC | ATC | AAA | CTC | 922 |
| Ala | Met | Asp | Glu | Asn | Ser | Glu | Lys | Lys | Arg | Lys | Arg | Ala | Ile | Lys | Leu | |
| | 275 | | | | | 280 | | | | | 285 | | | | | |
| ATT | GTC | ACT | GTC | CTG | GCC | ATG | TAC | CTG | ATC | TGC | TTC | ACT | CCT | AGT | AAC | 970 |
| Ile | Val | Thr | Val | Leu | Ala | Met | Tyr | Leu | Ile | Cys | Phe | Thr | Pro | Ser | Asn | |
| 290 | | | | | 295 | | | | | 300 | | | | | 305 | |
| CTT | CTG | CTT | GTG | GTG | CAT | TAT | TTT | CTG | ATT | AAG | AGC | CAG | GGC | CAG | AGC | 1018 |
| Leu | Leu | Leu | Val | Val | His | Tyr | Phe | Leu | Ile | Lys | Ser | Gln | Gly | Gln | Ser | |
| | | | | 310 | | | | | 315 | | | | | 320 | | |
| CAT | GTC | TAT | GCC | CTG | TAC | ATT | GTA | GCC | CTC | TGC | CTC | TCT | ACC | CTT | AAC | 1066 |
| His | Val | Tyr | Ala | Leu | Tyr | Ile | Val | Ala | Leu | Cys | Leu | Ser | Thr | Leu | Asn | |
| | | | 325 | | | | | 330 | | | | | 335 | | | |
| AGC | TGC | ATC | GAC | CCC | TTT | GTC | TAT | TAC | TTT | GTT | TCA | CAT | GAT | TTC | AGG | 1114 |
| Ser | Cys | Ile | Asp | Pro | Phe | Val | Tyr | Tyr | Phe | Val | Ser | His | Asp | Phe | Arg | |
| | | | 340 | | | | | 345 | | | | | 350 | | | |
| GAT | CAT | GCA | AAG | AAC | GCT | CTC | CTT | TGC | CGA | AGT | GTC | CGC | ACT | GTA | AAG | 1162 |
| Asp | His | Ala | Lys | Asn | Ala | Leu | Leu | Cys | Arg | Ser | Val | Arg | Thr | Val | Lys | |
| | | | 355 | | | | | 360 | | | | | 365 | | | |
| CAG | ATG | CAA | GTA | TCC | CTC | ACC | TCA | AAG | AAA | CAC | TCC | AGG | AAA | TCC | AGC | 1210 |
| Gln | Met | Gln | Val | Ser | Leu | Thr | Ser | Lys | Lys | His | Ser | Arg | Lys | Ser | Ser | |
| 370 | | | | | 375 | | | | | 380 | | | | | 385 | |

|     |     |     |     |     |     |     |     |     |     |     |     |     |     |     |     |
|-----|-----|-----|-----|-----|-----|-----|-----|-----|-----|-----|-----|-----|-----|-----|-----|
| TCT | TAC | TCT | TCA | AGT | TCA | ACC | ACT | GTT | AAG | ACC | TCC | TAT | TGAGTT |  | 1255 |
| Ser | Tyr | Ser | Ser | Ser | Ser | Thr | Thr | Val | Lys | Thr | Ser | Tyr |  |  |  |
|     |     |     |     | 390 |     |     |     |     | 395 |     |     |     |  |  |  |

( 2 ) INFORMATION FOR SEQ ID NO:4:

( i ) SEQUENCE CHARACTERISTICS:
        ( A ) LENGTH: 398 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| Met | Asn | Val | Leu | Ser | Phe | Glu | Gln | Thr | Ser | Val | Thr | Ala | Glu | Thr | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ile | Ser | Val | Met | Thr | Leu | Val | Phe | Leu | Ser | Cys | Thr | Gly | Thr | Asn | Arg |
|     |     |     | 20  |     |     |     |     | 25  |     |     |     |     | 30  |     |     |
| Ser | Ser | Lys | Gly | Arg | Ser | Leu | Ile | Gly | Lys | Val | Asp | Gly | Thr | Ser | His |
|     |     | 35  |     |     |     |     | 40  |     |     |     |     | 45  |     |     |     |
| Val | Thr | Gly | Lys | Gly | Val | Thr | Val | Glu | Thr | Val | Phe | Ser | Val | Asp | Glu |
|     | 50  |     |     |     |     | 55  |     |     |     |     | 60  |     |     |     |     |
| Phe | Ser | Ala | Ser | Val | Leu | Thr | Gly | Lys | Leu | Thr | Thr | Val | Phe | Leu | Pro |
| 65  |     |     |     |     | 70  |     |     |     |     | 75  |     |     |     |     | 80  |
| Ile | Val | Tyr | Thr | Ile | Val | Phe | Val | Val | Gly | Leu | Pro | Ser | Asn | Gly | Met |
|     |     |     |     | 85  |     |     |     |     | 90  |     |     |     |     | 95  |     |
| Ala | Leu | Trp | Val | Phe | Leu | Phe | Arg | Thr | Lys | Lys | Lys | His | Pro | Ala | Val |
|     |     |     | 100 |     |     |     |     | 105 |     |     |     |     | 110 |     |     |
| Ile | Tyr | Met | Ala | Asn | Leu | Ala | Leu | Ala | Asp | Leu | Leu | Ser | Val | Ile | Trp |
|     |     | 115 |     |     |     |     | 120 |     |     |     |     | 125 |     |     |     |
| Phe | Pro | Leu | Lys | Ile | Ala | Tyr | His | Ile | His | Gly | Asn | Asn | Trp | Ile | Tyr |
|     | 130 |     |     |     |     | 135 |     |     |     |     | 140 |     |     |     |     |
| Gly | Glu | Ala | Leu | Cys | Asn | Val | Leu | Ile | Gly | Phe | Phe | Tyr | Gly | Asn | Met |
| 145 |     |     |     |     | 150 |     |     |     |     | 155 |     |     |     |     | 160 |
| Tyr | Cys | Ser | Ile | Leu | Phe | Met | Thr | Cys | Leu | Ser | Val | Gln | Arg | Tyr | Trp |
|     |     |     |     | 165 |     |     |     |     | 170 |     |     |     |     | 175 |     |
| Val | Ile | Val | Asn | Pro | Met | Gly | His | Ser | Arg | Lys | Lys | Ala | Asn | Ile | Ala |
|     |     |     | 180 |     |     |     |     | 185 |     |     |     |     | 190 |     |     |
| Ile | Gly | Ile | Ser | Leu | Ala | Ile | Trp | Leu | Leu | Ile | Leu | Leu | Val | Thr | Ile |
|     |     | 195 |     |     |     |     | 200 |     |     |     |     | 205 |     |     |     |
| Pro | Leu | Tyr | Val | Val | Lys | Gln | Thr | Ile | Phe | Ile | Pro | Ala | Leu | Asn | Ile |
|     | 210 |     |     |     |     | 215 |     |     |     |     | 220 |     |     |     |     |
| Thr | Thr | Cys | His | Asp | Val | Leu | Pro | Glu | Gln | Leu | Leu | Val | Gly | Asp | Met |
| 225 |     |     |     |     | 230 |     |     |     |     | 235 |     |     |     |     | 240 |
| Phe | Asn | Tyr | Phe | Leu | Ser | Leu | Ala | Ile | Gly | Val | Phe | Leu | Phe | Pro | Ala |
|     |     |     |     | 245 |     |     |     |     | 250 |     |     |     |     | 255 |     |
| Phe | Leu | Thr | Ala | Ser | Ala | Tyr | Val | Leu | Met | Ile | Arg | Met | Leu | Arg | Ser |
|     |     |     | 260 |     |     |     |     | 265 |     |     |     |     | 270 |     |     |
| Ser | Ala | Met | Asp | Glu | Asn | Ser | Glu | Lys | Lys | Arg | Lys | Arg | Ala | Ile | Lys |
|     |     | 275 |     |     |     |     | 280 |     |     |     |     | 285 |     |     |     |
| Leu | Ile | Val | Thr | Val | Leu | Ala | Met | Tyr | Leu | Ile | Cys | Phe | Thr | Pro | Ser |
|     | 290 |     |     |     |     | 295 |     |     |     |     | 300 |     |     |     |     |
| Asn | Leu | Leu | Leu | Val | Val | His | Tyr | Phe | Leu | Ile | Lys | Ser | Gln | Gly | Gln |
| 305 |     |     |     |     | 310 |     |     |     |     | 315 |     |     |     |     | 320 |
| Ser | His | Val | Tyr | Ala | Leu | Tyr | Ile | Val | Ala | Leu | Cys | Leu | Ser | Thr | Leu |
|     |     |     |     | 325 |     |     |     |     | 330 |     |     |     |     | 335 |     |

```
Asn  Ser  Cys  Ile  Asp  Pro  Phe  Val  Tyr  Tyr  Phe  Val  Ser  His  Asp  Phe
               340                 345                           350

Arg  Asp  His  Ala  Lys  Asn  Ala  Leu  Leu  Cys  Arg  Ser  Val  Arg  Thr  Val
          355                      360                      365

Lys  Gln  Met  Gln  Val  Ser  Leu  Thr  Ser  Lys  Lys  His  Ser  Arg  Lys  Ser
     370                      375                      380

Ser  Ser  Tyr  Ser  Ser  Ser  Ser  Thr  Thr  Val  Lys  Thr  Ser  Tyr
385                      390                      395
```

( 2 ) INFORMATION FOR SEQ ID NO:5:

( i ) SEQUENCE CHARACTERISTICS:
        ( A ) LENGTH: 395 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Met  Phe  His  Leu  Lys  His  Ser  Ser  Leu  Thr  Val  Gly  Pro  Phe  Ile  Ser
1                   5                        10                      15

Val  Met  Ile  Leu  Leu  Arg  Phe  Leu  Cys  Thr  Gly  Arg  Asn  Asn  Ser  Lys
               20                      25                      30

Gly  Arg  Ser  Leu  Ile  Gly  Arg  Leu  Glu  Thr  Gln  Pro  Pro  Ile  Thr  Gly
          35                      40                      45

Lys  Gly  Val  Pro  Val  Glu  Pro  Gly  Phe  Ser  Ile  Asp  Glu  Phe  Ser  Ala
     50                      55                      60

Ser  Ile  Leu  Thr  Gly  Lys  Leu  Thr  Thr  Val  Phe  Leu  Pro  Val  Val  Tyr
65                       70                      75                      80

Ile  Ile  Val  Phe  Val  Ile  Gly  Leu  Pro  Ser  Asn  Gly  Met  Ala  Leu  Trp
                    85                      90                      95

Ile  Phe  Leu  Phe  Arg  Thr  Lys  Lys  Lys  His  Pro  Ala  Val  Ile  Tyr  Met
                    100                     105                     110

Ala  Asn  Leu  Ala  Leu  Ala  Asp  Leu  Leu  Ser  Val  Ile  Trp  Phe  Pro  Leu
               115                     120                     125

Lys  Ile  Ser  Tyr  His  Leu  His  Gly  Asn  Asn  Trp  Val  Tyr  Gly  Glu  Ala
     130                     135                     140

Leu  Cys  Lys  Val  Leu  Ile  Gly  Phe  Phe  Tyr  Gly  Asn  Met  Tyr  Cys  Ser
145                     150                     155                     160

Ile  Leu  Phe  Met  Thr  Cys  Leu  Ser  Val  Gln  Arg  Tyr  Trp  Val  Ile  Val
               165                     170                     175

Asn  Pro  Met  Gly  His  Pro  Arg  Lys  Lys  Ala  Asn  Ile  Ala  Val  Gly  Val
          180                     185                     190

Ser  Leu  Ala  Ile  Trp  Leu  Leu  Ile  Phe  Leu  Val  Thr  Ile  Pro  Leu  Tyr
     195                     200                     205

Val  Met  Lys  Gln  Thr  Ile  Tyr  Ile  Pro  Ala  Leu  Asn  Ile  Thr  Thr  Cys
     210                     215                     220

His  Asp  Val  Leu  Pro  Glu  Glu  Val  Leu  Val  Gly  Asp  Met  Phe  Asn  Tyr
225                     230                     235                     240

Phe  Leu  Ser  Leu  Ala  Ile  Gly  Val  Phe  Leu  Phe  Pro  Ala  Leu  Leu  Thr
               245                     250                     255

Ala  Ser  Ala  Tyr  Val  Leu  Met  Ile  Lys  Thr  Leu  Arg  Ser  Ser  Ala  Met
               260                     265                     270

Asp  Glu  His  Ser  Glu  Lys  Lys  Arg  Gln  Arg  Ala  Ile  Arg  Leu  Ile  Ile
          275                     280                     285

Thr  Val  Leu  Ala  Met  Tyr  Phe  Ile  Cys  Phe  Ala  Pro  Ser  Asn  Leu  Leu
     290                     295                     300
```

| Leu | Val | Val | His | Tyr | Phe | Leu | Ile | Lys | Thr | Gln | Arg | Gln | Ser | His | Val |
| 305 | | | | 310 | | | | | 315 | | | | | | 320 |

| Tyr | Ala | Leu | Tyr | Leu | Val | Ala | Leu | Cys | Leu | Ser | Thr | Leu | Asn | Ser | Cys |
| | | | | 325 | | | | | 330 | | | | | 335 | |

| Ile | Asp | Pro | Phe | Val | Tyr | Tyr | Phe | Val | Ser | Lys | Asp | Phe | Arg | Asp | His |
| | | | 340 | | | | | 345 | | | | | 350 | | |

| Ala | Arg | Asn | Ala | Leu | Leu | Cys | Arg | Ser | Val | Arg | Thr | Val | Asn | Arg | Met |
| | | | 355 | | | | | 360 | | | | | 365 | | |

| Gln | Ile | Ser | Leu | Ser | Ser | Asn | Lys | Phe | Ser | Arg | Lys | Ser | Cys | Ser | Tyr |
| | | 370 | | | | | 375 | | | | | 380 | | | |

| Ser | Ser | Ser | Ser | Thr | Ser | Val | Lys | Thr | Ser | Tyr | | | | | |
| 385 | | | | | 390 | | | | | 395 | | | | | |

( 2 ) INFORMATION FOR SEQ ID NO:6:

( i ) SEQUENCE CHARACTERISTICS:
( A ) LENGTH: 398 amino acids
( B ) TYPE: amino acid
( C ) STRANDEDNESS: single
( D ) TOPOLOGY: linear ( x i ) SEQUENCE DESCRIPTION: SEQ ID NO:6:

| Met | Asn | Val | Leu | Ser | Phe | Glu | Gln | Thr | Ser | Val | Thr | Ala | Glu | Thr | Phe |
| 1 | | | | 5 | | | | | 10 | | | | | 15 | |

| Ile | Ser | Val | Met | Ile | Leu | Val | Phe | Leu | Ser | Cys | Thr | Gly | Thr | Asn | Arg |
| | | | 20 | | | | | 25 | | | | | 30 | | |

| Ser | Ser | Lys | Gly | Arg | Ser | Leu | Ile | Gly | Lys | Val | Asp | Gly | Thr | Ser | His |
| | | 35 | | | | | 40 | | | | | 45 | | | |

| Val | Thr | Gly | Lys | Gly | Val | Ile | Val | Glu | Ile | Val | Phe | Ser | Val | Asp | Glu |
| | 50 | | | | | 55 | | | | | 60 | | | | |

| Phe | Ser | Ala | Ser | Val | Leu | Thr | Gly | Lys | Leu | Thr | Thr | Val | Phe | Leu | Pro |
| 65 | | | | | 70 | | | | | 75 | | | | | 80 |

| Ile | Val | Tyr | Ile | Ile | Val | Phe | Val | Val | Gly | Leu | Pro | Ser | Asn | Gly | Met |
| | | | | 85 | | | | | 90 | | | | | 95 | |

| Ala | Leu | Trp | Val | Phe | Leu | Phe | Arg | Thr | Lys | Lys | Lys | His | Pro | Ala | Val |
| | | | 100 | | | | | 105 | | | | | 110 | | |

| Ile | Tyr | Met | Ala | Asn | Leu | Ala | Leu | Ala | Asp | Leu | Leu | Ser | Val | Ile | Trp |
| | | | 115 | | | | | 120 | | | | | 125 | | |

| Phe | Pro | Leu | Lys | Ile | Ala | Tyr | His | Ile | His | Gly | Asn | Asn | Trp | Ile | Tyr |
| | | 130 | | | | | 135 | | | | | 140 | | | |

| Gly | Glu | Ala | Leu | Cys | Asn | Val | Leu | Ile | Gly | Phe | Phe | Tyr | Gly | Asn | Met |
| 145 | | | | | 150 | | | | | 155 | | | | | 160 |

| Tyr | Cys | Ser | Ile | Leu | Phe | Met | Thr | Cys | Leu | Ser | Val | Gln | Arg | Tyr | Trp |
| | | | | 165 | | | | | 170 | | | | | 175 | |

| Val | Ile | Val | Asn | Pro | Met | Gly | His | Ser | Arg | Lys | Lys | Ala | Asn | Ile | Ala |
| | | | 180 | | | | | 185 | | | | | 190 | | |

| Ile | Gly | Ile | Ser | Leu | Ala | Ile | Trp | Leu | Leu | Ile | Leu | Leu | Val | Thr | Ile |
| | | 195 | | | | | 200 | | | | | 205 | | | |

| Pro | Leu | Tyr | Val | Val | Lys | Gln | Thr | Ile | Phe | Ile | Pro | Ala | Leu | Asn | Ile |
| | 210 | | | | | 215 | | | | | 220 | | | | |

| Thr | Thr | Cys | His | Asp | Val | Leu | Pro | Glu | Gln | Val | Leu | Val | Gly | Asp | Met |
| 225 | | | | | 230 | | | | | 235 | | | | | 240 |

| Phe | Asn | Tyr | Phe | Leu | Ser | Leu | Ala | Ile | Gly | Val | Phe | Leu | Phe | Pro | Ala |
| | | | | 245 | | | | | 250 | | | | | 255 | |

| Phe | Leu | Thr | Ala | Ser | Ala | Tyr | Val | Leu | Met | Ile | Arg | Met | Leu | Arg | Ser |
| | | | 260 | | | | | 265 | | | | | 270 | | |

```
Ser  Ala  Met  Asp  Glu  Asn  Ser  Glu  Lys  Lys  Arg  Lys  Arg  Ala  Ile  Lys
          275                      280                    285

Leu  Ile  Val  Thr  Val  Leu  Ala  Met  Tyr  Leu  Ile  Cys  Phe  Ile  Pro  Ser
     290                      295                    300

Asn  Leu  Leu  Leu  Val  Val  His  Tyr  Phe  Leu  Ile  Lys  Ser  Gln  Gly  Gln
305                           310                    315                      320

Ser  His  Val  Tyr  Ala  Leu  Tyr  Ile  Val  Ala  Leu  Cys  Leu  Ser  Thr  Leu
                    325                      330                          335

Asn  Ser  Cys  Ile  Asp  Pro  Phe  Val  Tyr  Tyr  Phe  Val  Ser  His  Asp  Phe
               340                      345                         350

Arg  Asp  His  Ala  Lys  Asn  Ala  Leu  Leu  Cys  Arg  Ser  Val  Arg  Thr  Val
          355                      360                         365

Lys  Gln  Met  Gln  Val  Ser  Leu  Ile  Ser  Lys  Lys  His  Ser  Arg  Lys  Ser
370                      375                         380

Ser  Ser  Tyr  Ser  Ser  Ser  Ser  Thr  Ile  Val  Lys  Thr  Ser  Tyr
385                      390                      395
```

( 2 ) INFORMATION FOR SEQ ID NO:7:

( i ) SEQUENCE CHARACTERISTICS:
        ( A ) LENGTH: 425 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
Met  Gly  Pro  Arg  Arg  Leu  Leu  Leu  Val  Ala  Ala  Cys  Phe  Ser  Leu  Cys
1                   5                        10                         15

Gly  Phe  Leu  Leu  Ser  Ala  Arg  Thr  Arg  Ala  Arg  Arg  Pro  Glu  Ser  Lys
               20                      25                         30

Ala  Thr  Asn  Ala  Thr  Leu  Asp  Pro  Arg  Ser  Phe  Leu  Leu  Arg  Asn  Pro
          35                       40                       45

Asn  Asp  Lys  Tyr  Glu  Pro  Phe  Trp  Glu  Asp  Glu  Lys  Asn  Glu  Ser
     50                       55                       60

Gly  Leu  Thr  Glu  Tyr  Arg  Leu  Val  Ser  Ile  Asn  Lys  Ser  Ser  Pro  Leu
65                        70                        75                        80

Gln  Lys  Gln  Leu  Pro  Ala  Phe  Ile  Ser  Glu  Asp  Ala  Ser  Gly  Tyr  Leu
                    85                       90                            95

Thr  Ser  Ser  Trp  Leu  Thr  Leu  Phe  Val  Pro  Ser  Val  Tyr  Thr  Gly  Val
               100                      105                         110

Phe  Val  Val  Ser  Leu  Pro  Leu  Asn  Ile  Met  Ala  Ile  Val  Val  Phe  Ile
          115                      120                         125

Leu  Lys  Met  Lys  Val  Lys  Lys  Pro  Ala  Val  Val  Tyr  Met  Leu  His  Leu
     130                     135                          140

Ala  Thr  Ala  Asp  Val  Leu  Phe  Val  Ser  Val  Leu  Pro  Phe  Lys  Ile  Ser
145                      150                      155                      160

Tyr  Tyr  Phe  Ser  Gly  Ser  Asp  Trp  Gln  Phe  Gly  Ser  Glu  Leu  Cys  Arg
               165                      170                         175

Phe  Val  Thr  Ala  Ala  Phe  Tyr  Cys  Asn  Met  Tyr  Ala  Ser  Ile  Leu  Leu
          180                      185                         190

Met  Thr  Val  Ile  Ser  Ile  Asp  Arg  Phe  Leu  Ala  Val  Val  Tyr  Pro  Met
     195                     200                          205

Gln  Ser  Leu  Ser  Trp  Arg  Thr  Leu  Gly  Arg  Ala  Ser  Phe  Thr  Cys  Leu
          210                      215                         220

Ala  Ile  Trp  Ala  Leu  Ala  Ile  Ala  Gly  Val  Val  Pro  Leu  Val  Leu  Lys
225                      230                      235                      240
```

| | | | | | | | | | | | | | | |
|---|---|---|---|---|---|---|---|---|---|---|---|---|---|---|
| Glu | Gln | Thr | Ile | Gln 245 | Val | Pro | Gly | Leu | Asn 250 | Ile | Thr | Thr | Cys | His 255 | Asp |
| Val | Leu | Asn | Glu 260 | Thr | Leu | Leu | Glu | Gly 265 | Tyr | Tyr | Ala | Tyr | Tyr 270 | Phe | Ser |
| Ala | Phe | Ser 275 | Ala | Val | Phe | Phe 280 | Val | Pro | Leu | Ile | Ile 285 | Ser | Thr | Val |
| Cys | Tyr 290 | Val | Ser | Ile | Ile | Arg 295 | Cys | Leu | Ser | Ser | Ser 300 | Ala | Val | Ala | Asn |
| Arg 305 | Ser | Lys | Lys | Ser | Arg 310 | Ala | Leu | Phe | Leu | Ser 315 | Ala | Ala | Val | Phe | Cys 320 |
| Ile | Phe | Ile | Ile | Cys 325 | Phe | Gly | Pro | Thr | Asn 330 | Val | Leu | Leu | Ile | Ala | His 335 |
| Tyr | Ser | Phe | Leu 340 | Ser | His | Thr | Ser | Thr 345 | Thr | Glu | Ala | Ala | Tyr 350 | Phe | Ala |
| Tyr | Leu | Leu 355 | Cys | Val | Cys | Val | Ser 360 | Ser | Ile | Ser | Ser | Cys 365 | Ile | Asp | Pro |
| Leu | Ile 370 | Tyr | Tyr | Tyr | Ala | Ser 375 | Ser | Glu | Cys | Gln | Arg 380 | Tyr | Val | Tyr | Ser |
| Ile 385 | Leu | Cys | Cys | Lys | Glu 390 | Ser | Ser | Asp | Pro | Ser 395 | Ser | Tyr | Asn | Ser | Ser 400 |
| Gly | Gln | Leu | Met | Ala 405 | Ser | Lys | Met | Asp | Thr 410 | Cys | Ser | Ser | Asn | Leu 415 | Asn |
| Asn | Ser | Ile | Tyr 420 | Lys | Lys | Leu | Leu | Thr 425 | | | | | | | |

( 2 ) INFORMATION FOR SEQ ID NO:8:

( i ) SEQUENCE CHARACTERISTICS:
       ( A ) LENGTH: 7 amino acids
       ( B ) TYPE: amino acid
       ( C ) STRANDEDNESS: single
       ( D ) TOPOLOGY: linear ( x i ) SEQUENCE DESCRIPTION: SEQ ID NO:8:

| Arg | Asn | Asn | Ser | Lys | Gly | Arg |
|---|---|---|---|---|---|---|
| 1 | | | | 5 | | |

( 2 ) INFORMATION FOR SEQ ID NO:9:

( i ) SEQUENCE CHARACTERISTICS:
       ( A ) LENGTH: 5 amino acids
       ( B ) TYPE: amino acid
       ( C ) STRANDEDNESS: single
       ( D ) TOPOLOGY: linear ( i x ) FEATURE:
       ( A ) NAME/KEY: Modified-site
       ( B ) LOCATION: 1
       ( D ) OTHER INFORMATION: /note="This position is Mpr = 3- mercaptopropionic acid."

( x i ) SEQUENCE DESCRIPTION: SEQ ID NO:9:

| Xaa | Leu | Leu | Gly | Lys |
|---|---|---|---|---|
| 1 | | | | 5 |

( 2 ) INFORMATION FOR SEQ ID NO:10:

( i ) SEQUENCE CHARACTERISTICS:
       ( A ) LENGTH: 5 amino acids
       ( B ) TYPE: amino acid
       ( C ) STRANDEDNESS: single ( i x ) FEATURE:

(A) NAME/KEY: Modified-site
(B) LOCATION: 1
(D) OTHER INFORMATION: /note="This position is Mpr = 3- mercaptopropionic acid."

(x i) SEQUENCE DESCRIPTION: SEQ ID NO:10:

Xaa Leu Ile Gly Arg
1             5

(2) INFORMATION FOR SEQ ID NO:11:

(i) SEQUENCE CHARACTERISTICS:
    (A) LENGTH: 5 amino acids
    (B) TYPE: amino acid
    (C) STRANDEDNESS: single
    (D) TOPOLOGY: linear (i x) FEATURE:
    (A) NAME/KEY: Modified-site
    (B) LOCATION: 1
    (D) OTHER INFORMATION: /note="This position is Mpr = 3- mercaptopropionic acid."

(i x) FEATURE:
    (A) NAME/KEY: Modified-site
    (B) LOCATION: 2
    (D) OTHER INFORMATION: /note="This position is Cha = cyclohexylalanine."

(x i) SEQUENCE DESCRIPTION: SEQ ID NO:11:

Xaa Xaa Leu Lys Gly
1             5

(2) INFORMATION FOR SEQ ID NO:12:

(i) SEQUENCE CHARACTERISTICS:
    (A) LENGTH: 5 amino acids
    (B) TYPE: amino acid
    (C) STRANDEDNESS: single
    (D) TOPOLOGY: linear (i x) FEATURE:
    (A) NAME/KEY: Modified-site
    (B) LOCATION: 1
    (D) OTHER INFORMATION: /note="This position is Mpr = 3- mercaptopropionic acid."

(i x) FEATURE:
    (A) NAME/KEY: Modified-site
    (B) LOCATION: 2
    (D) OTHER INFORMATION: /note="This position is (Cha) = cyclohexylalanine."

(x i) SEQUENCE DESCRIPTION: SEQ ID NO:12:

Xaa Xaa Ile Gly Arg
1             5

(2) INFORMATION FOR SEQ ID NO:13:

(i) SEQUENCE CHARACTERISTICS:
    (A) LENGTH: 6 amino acids
    (B) TYPE: amino acid
    (C) STRANDEDNESS: single
    (D) TOPOLOGY: linear (i x) FEATURE:
    (A) NAME/KEY: Modified-site
    (B) LOCATION: 1
    (D) OTHER INFORMATION: /note="This position is Mpr = 3- mercaptopropionic acid."

(x i) SEQUENCE DESCRIPTION: SEQ ID NO:13:

Xaa Leu Leu Gly Lys Lys 1          5

(2) INFORMATION FOR SEQ ID NO:14:

(i) SEQUENCE CHARACTERISTICS:
        (A) LENGTH: 6 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note="This position is Mpr =
            3- mercaptopropionic acid."

(xi) SEQUENCE DESCRIPTION: SEQ ID NO:14:

Xaa Leu Ile Gly Arg Lys
1                 5

(2) INFORMATION FOR SEQ ID NO:15:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note="This position is Mpr =
            3- mercaptopropionic acid."

(xi) SEQUENCE DESCRIPTION: SEQ ID NO:15:

Xaa Leu Ile Gly Arg Lys Glu Thr Gln Pro
1                 5                   10

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note="This position is Mpr =
            3- mercaptopropionic acid."

(xi) SEQUENCE DESCRIPTION: SEQ ID NO:16:

Xaa Leu Leu Gly Lys Lys Asp Gly Thr Ser
1                 5                   10

(2) INFORMATION FOR SEQ ID NO:17:

(i) SEQUENCE CHARACTERISTICS:
        (A) LENGTH: 5 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 1
        (D) OTHER INFORMATION: /note="This position is
            (n-pentyl)2-N-Leu."

(xi) SEQUENCE DESCRIPTION: SEQ ID NO:17:

Xaa Ile Gly Arg Lys (2) INFORMATION FOR SEQ ID NO:18:

(i) SEQUENCE CHARACTERISTICS:
  (A) LENGTH: 6 amino acids
  (B) TYPE: amino acid
  (C) STRANDEDNESS: single
  (D) TOPOLOGY: linear (ix) FEATURE:
  (A) NAME/KEY: Modified-site
  (B) LOCATION: 1
  (D) OTHER INFORMATION: /note="This position is (Me - N - ( n-pentyl)."

(xi) SEQUENCE DESCRIPTION: SEQ ID NO:18:

```
Xaa Leu Ile Gly Arg Lys
1               5
```

(2) INFORMATION FOR SEQ ID NO:19:

(i) SEQUENCE CHARACTERISTICS:
  (A) LENGTH: 12 amino acids
  (B) TYPE: amino acid
  (C) STRANDEDNESS: single
  (D) TOPOLOGY: linear (xi) SEQUENCE DESCRIPTION: SEQ ID NO:19:

```
Ser Lys Gly Arg Ser Leu Ile Gly Arg Leu Glu Thr
1               5                   10
```

(2) INFORMATION FOR SEQ ID NO:20:

(i) SEQUENCE CHARACTERISTICS:
  (A) LENGTH: 17 amino acids
  (B) TYPE: amino acid
  (C) STRANDEDNESS: single
  (D) TOPOLOGY: linear (xi) SEQUENCE DESCRIPTION: SEQ ID NO:20:

```
Ile Ser Tyr His Leu His Gly Asn Asn Trp Val Tyr Gly Glu Ala Leu
1               5                   10                  15
Cys
```

(2) INFORMATION FOR SEQ ID NO:21:

(i) SEQUENCE CHARACTERISTICS:
  (A) LENGTH: 31 amino acids
  (B) TYPE: amino acid
  (C) STRANDEDNESS: single
  (D) TOPOLOGY: linear (xi) SEQUENCE DESCRIPTION: SEQ ID NO:21:

```
Gln Thr Ile Tyr Ile Pro Ala Leu Asn Ile Thr Thr Cys His Asp Val
1               5                   10                  15
Leu Pro Glu Glu Val Leu Val Gly Asp Met Phe Asn Tyr Phe Leu
                20                  25                  30
```

(2) INFORMATION FOR SEQ ID NO:22:

(i) SEQUENCE CHARACTERISTICS:
  (A) LENGTH: 15 amino acids
  (B) TYPE: amino acid
  (C) STRANDEDNESS: single
  (D) TOPOLOGY: linear (xi) SEQUENCE DESCRIPTION: SEQ ID NO:22:

```
        His  Tyr  Phe  Leu  Ile  Lys  Thr  Gln  Arg  Gln  Ser  His  Val  Tyr  Ala
        1              5                        10                       15
```

(2) INFORMATION FOR SEQ ID NO:23:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:23:

```
        Ser  Leu  Ile  Gly  Arg  Leu
        1              5
```

(2) INFORMATION FOR SEQ ID NO:24:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:24:

```
        Ser  Leu  Ile  Gly  Arg  Ala
        1              5
```

(2) INFORMATION FOR SEQ ID NO:25:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:25:

```
        Ser  Leu  Ile  Gly  Ala  Leu
        1              5
```

(2) INFORMATION FOR SEQ ID NO:26:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:26:

```
        Ser  Leu  Ile  Ala  Arg  Leu
        1              5
```

(2) INFORMATION FOR SEQ ID NO:27:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:27:

```
        Ser  Leu  Ala  Gly  Arg  Leu
        1              5
```

(2) INFORMATION FOR SEQ ID NO:28:

(i) SEQUENCE CHARACTERISTICS:
        (A) LENGTH: 6 amino acids
        (B) TYPE: amino acid
        (C) STRANDEDNESS: single ( D ) TOPOLOGY: linear ( x i ) SEQUENCE DESCRIPTION: SEQ ID NO:28:

Ser Ala Ile Gly Arg Leu
1               5

( 2 ) INFORMATION FOR SEQ ID NO:29:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:29:

Ala Leu Ile Gly Arg Leu
1               5

( 2 ) INFORMATION FOR SEQ ID NO:30:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:30:

Ser Phe Phe Leu Arg Trp
1               5

( 2 ) INFORMATION FOR SEQ ID NO:31:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:31:

Arg Asn Asn Ser Ser Lys Gly Arg
1               5

( 2 ) INFORMATION FOR SEQ ID NO:32:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( x i ) SEQUENCE DESCRIPTION: SEQ ID NO:32:

Ser Leu Ile Gly Arg Leu Glu Thr Gln Pro Pro Ile Thr
1               5                   10

( 2 ) INFORMATION FOR SEQ ID NO:33:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:33:

Ser Leu Ile Gly Arg Leu Glu Thr Gln Pro Pro Ile
1               5                   10

( 2 ) INFORMATION FOR SEQ ID NO:34:

( i ) SEQUENCE CHARACTERISTICS:
   ( A ) LENGTH: 11 amino acids
   ( B ) TYPE: amino acid
   ( C ) STRANDEDNESS: single
   ( D ) TOPOLOGY: linear ( x i ) SEQUENCE DESCRIPTION: SEQ ID NO:34:

Ser Leu Ile Gly Arg Leu Glu Thr Gln Pro Pro
1               5                   10

( 2 ) INFORMATION FOR SEQ ID NO:35:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( x i ) SEQUENCE DESCRIPTION: SEQ ID NO:35:

Ser Leu Ile Gly Arg Leu Glu Thr Gln Pro
1               5                   10

( 2 ) INFORMATION FOR SEQ ID NO:36:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( x i ) SEQUENCE DESCRIPTION: SEQ ID NO:36:

Ser Leu Ile Gly Arg Leu Glu Thr Gln
1               5

( 2 ) INFORMATION FOR SEQ ID NO:37:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:37:

Ser Leu Ile Gly Arg Leu Glu Thr
1               5

( 2 ) INFORMATION FOR SEQ ID NO:38:

( i ) SEQUENCE CHARACTERISTICS:
      ( A ) LENGTH: 7 amino acids
      ( B ) TYPE: amino acid
      ( C ) STRANDEDNESS: single
      ( D ) TOPOLOGY: linear ( x i ) SEQUENCE DESCRIPTION: SEQ ID NO:38:

Ser Leu Ile Gly Arg Leu Glu
1               5

( 2 ) INFORMATION FOR SEQ ID NO:39:

( i ) SEQUENCE CHARACTERISTICS:
      ( A ) LENGTH: 6 amino acids
      ( B ) TYPE: amino acid
      ( C ) STRANDEDNESS: single
      ( D ) TOPOLOGY: linear ( x i ) SEQUENCE DESCRIPTION: SEQ ID NO:39:

Ser Leu Ile Gly Arg Leu
1               5

( 2 ) INFORMATION FOR SEQ ID NO:40:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:40:

```
Ser  Leu  Ile  Gly  Arg
1                    5
```

( 2 ) INFORMATION FOR SEQ ID NO:41:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( x i ) SEQUENCE DESCRIPTION: SEQ ID NO:41:

```
Ser  Leu  Leu  Gly  Lys  Val  Asp  Gly  Thr  Ser  His  Val  Thr
1                    5                        10
```

( 2 ) INFORMATION FOR SEQ ID NO:42:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:42:

```
Ser  Leu  Leu  Gly  Lys  Val  Asp  Gly  Thr  Ser  His  Val
1                    5                        10
```

( 2 ) INFORMATION FOR SEQ ID NO:43:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( x i ) SEQUENCE DESCRIPTION: SEQ ID NO:43:

```
Ser  Leu  Leu  Gly  Lys  Val  Asp  Gly  Thr  Ser  His
1                    5                        10
```

( 2 ) INFORMATION FOR SEQ ID NO:44:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:44:

```
Ser  Leu  Leu  Gly  Lys  Val  Asp  Gly  Thr  Ser
1                    5                        10
```

( 2 ) INFORMATION FOR SEQ ID NO:45:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( x i ) SEQUENCE DESCRIPTION: SEQ ID NO:45:

Ser Leu Leu Gly Lys Val Asp Gly Thr
1               5

( 2 ) INFORMATION FOR SEQ ID NO:46:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( x i ) SEQUENCE DESCRIPTION: SEQ ID NO:46:

Ser Leu Leu Gly Lys Val Asp Gly
1               5

( 2 ) INFORMATION FOR SEQ ID NO:47:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( x i ) SEQUENCE DESCRIPTION: SEQ ID NO:47:

Ser Leu Leu Gly Lys Val Asp
1               5

( 2 ) INFORMATION FOR SEQ ID NO:48:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:48:

Ser Leu Leu Gly Lys Val
1               5

( 2 ) INFORMATION FOR SEQ ID NO:49:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:49:

Ser Leu Leu Gly Lys
1               5

( 2 ) INFORMATION FOR SEQ ID NO:50:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 2
        ( D ) OTHER INFORMATION: /note="This position is (Cha) = cyclohexylalanine."

( x i ) SEQUENCE DESCRIPTION: SEQ ID NO:50:

Ser Xaa Ile Gly Arg
1               5

( 2 ) INFORMATION FOR SEQ ID NO:51:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 2
( D ) OTHER INFORMATION: /note="This position is (Cha) = cyclohexylalanine."

( x i ) SEQUENCE DESCRIPTION: SEQ ID NO:51:

Ser Xaa Leu Gly Lys
1               5

( 2 ) INFORMATION FOR SEQ ID NO:52:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note="This position is (2,3-diaP) = 2,3-diamino propionic."

( x i ) SEQUENCE DESCRIPTION: SEQ ID NO:52:

Xaa Ile Gly Arg
1

( 2 ) INFORMATION FOR SEQ ID NO:53:

( i ) SEQUENCE CHARACTERISTICS:
( A ) LENGTH: 5 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note="This position is (2,3-diaP) = 2,3-diamino propionic."

( x i ) SEQUENCE DESCRIPTION: SEQ ID NO:53:

Xaa Leu Leu Gly Lys
1               5

( 2 ) INFORMATION FOR SEQ ID NO:54:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( x i ) SEQUENCE DESCRIPTION: SEQ ID NO:54:

Ser Leu Leu Gly Lys Arg
1               5

( 2 ) INFORMATION FOR SEQ ID NO:55:

( i ) SEQUENCE CHARACTERISTICS:
( A ) LENGTH: 6 amino acids (B) TYPE: amino acid
(C) STRANDEDNESS: single
(D) TOPOLOGY: linear (xi) SEQUENCE DESCRIPTION: SEQ ID NO:55:

Ser Leu Ile Gly Arg Arg
1               5

(2) INFORMATION FOR SEQ ID NO:56:

(i) SEQUENCE CHARACTERISTICS:
    (A) LENGTH: 6 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 2
    (D) OTHER INFORMATION: /note="This position is (Cha) = cyclohexylalanine."

(xi) SEQUENCE DESCRIPTION: SEQ ID NO:56:

Ser Xaa Leu Gly Lys Lys
1               5

(2) INFORMATION FOR SEQ ID NO:57:

(i) SEQUENCE CHARACTERISTICS:
    (A) LENGTH: 6 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 2
    (D) OTHER INFORMATION: /note="This position is (Cha) = cyclohexylalanine."

(xi) SEQUENCE DESCRIPTION: SEQ ID NO:57:

Ser Xaa Ile Gly Arg Lys
1               5

(2) INFORMATION FOR SEQ ID NO:58:

(i) SEQUENCE CHARACTERISTICS:
    (A) LENGTH: 6 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /note="This position is (2,3-diaP) = 2,3-diamino propionic."

(xi) SEQUENCE DESCRIPTION: SEQ ID NO:58:

Xaa Leu Ile Gly Arg Lys
1               5

(2) INFORMATION FOR SEQ ID NO:59:

(i) SEQUENCE CHARACTERISTICS:
    (A) LENGTH: 6 amino acids
    (B) TYPE: amino acid
    (C) STRANDEDNESS: single
    (D) TOPOLOGY: linear (ix) FEATURE:
    (A) NAME/KEY: Modified-site -continued ( B ) LOCATION: 1
( D ) OTHER INFORMATION: /note="This position is (2,3-diaP)
    =    2,3-diamino propionic."

( x i ) SEQUENCE DESCRIPTION: SEQ ID NO:59:

Xaa  Leu  Leu  Gly  Lys  Lys
1                 5

RECOMBINANT C140 RECEPTOR

TECHNICAL FIELD

The invention relates to a newly discovered receptor which is a member of the G-protein-coupled receptor superfamily. The receptor is expressed in endothelial cells in blood vessels. Avoidance of affects on this receptor is an essential element in limiting side effects of drugs which are administered to stimulate other receptors in this family.

BACKGROUND ART

Responses of animals to many therapeutic and prophylactic drugs are mediated through receptors which reside on cell surfaces. One class of such receptors comprises the G-protein-coupled receptors, whose physiological effect is mediated by a three-subunit protein complex, called G-proteins, that binds to this type of receptor with the subsequent release of a subunit, thus setting in motion additional intracellular events. Receptors of this subclass include, among others, adrenergic receptors, neuropeptide receptors, the thrombin receptor and the C140 receptor which is the subject of the herein invention. This class of receptor is characterized by the presence of seven transmembrane regions which anchor the receptor within the cell surface.

It is the elusive goal of the designers of therapeutic substances to effect a desired response in a subject in the absence of side effects. Accordingly, pharmaceuticals designed to target a specific receptor, such as the thrombin receptor, should react with the thrombin receptor specifically and have no effect on related receptors. The C140 receptor of the present invention may be involved in controlling vascular pressure, and inadvertent stimulation or blocking of this receptor would have unpredictable and therefore undesirable results. It is therefore useful to determine in advance whether therapeutic reagents designed to target, for example, the thrombin receptor will or will not have the undesired side effect of reactivity with the C140 receptor. By providing the recombinant materials for the production of the C140 receptor in convenient assay systems, as well as agonist and antagonist reagents for use in this assay, the invention makes possible the prior determination of the presence or absence of the side effect of reactivity with the C140 receptor in candidate pharmaceuticals. This side effect will usually be undesired as it is believed that the C140 receptor responds to enzymes such as serine proteases associated with trauma and immune disturbances.

DISCLOSURE OF THE INVENTION

The invention provides methods and materials useful in assay systems to determine the propensity of candidate pharmaceuticals to exert undesirable side effects. The isolation, recombinant production and characterization of the C140 receptor permits the design of assay systems using the receptor as a substrate and using agonists and antagonists for the receptor as control reagents in the assay.

Thus, in one aspect, the invention is directed to recombinant materials associated with the production of C140 receptor. These include, for example, transfected cells which can be cultured so as to display the C140 receptor on their surfaces, and thus provide an assay system for the interaction of materials with the native C140 receptor. In general, the limitations on the host cells useful in these assay systems are that the cells have the appropriate mechanism to display the receptor on their surfaces and contain the G-protein as mediator to the intracellular response. (However assays which merely assess binding do not require the G-protein.) Most animal cells meet these requirements.

In another aspect, the invention is directed to C140 receptor agonists which mimic the activated form of the extracellular portion of the receptor protein. These agonists are useful as control reagents in the above-mentioned assays to verify the workability of the assay system. In addition, agonists for the C140 receptor may exhibit hypotensive effects in vivo. Accordingly, the agonists may be also, themselves, useful as antihypertensives.

In still another aspect, the invention is directed to C140 receptor antagonists. These antagonists comprise modified forms of the C140 receptor agonist peptides that lack the essential features required for activation of the receptor. These antagonists bind to receptor, do not activate it, and prevent receptor activation by agonists and the native receptor-binding ligand.

A second group of antagonists includes antibodies designed to bind specific portions of the receptor protein. In general, these are monoclonal antibody preparations which are highly specific for any desired region of the C140 receptor. The antibodies of the invention are also useful in immunoassays for the receptor protein, for example, in assessing successful expression of the gene in recombinant systems.

In another aspect, the invention is related to assay systems which utilize recombinant C140 receptor to screen for agonist and antagonist activity of candidate drugs. This assay is especially useful in assuring that these therapeutic agents do not have undesired side effects caused by activation or inhibition of the C140 receptor. In some cases agonist activity at this receptor system may have therapeutic utility. Some of these assay systems include the use of the agonist peptides as positive controls. The assay can also be used to screen for antagonists which inhibit the agonistic effect.

Another aspect of the invention relates to the diagnosis of conditions characterized by activation of the C140 receptor by detection in fluids, such as blood or urine, of the peptide cleaved from the C140 receptor when the receptor is activated. Another diagnostic method included in the invention is visualization of the activated forms of receptor by localizing an imaging agent to activated receptor in situ using antibodies specific to the activated receptor.

Additional aspects of the invention are directed to pharmaceutical compositions containing the agonists and antagonists of the invention. The agonists of the invention are antihypertensives; conversely, the antagonists can elevate blood pressure if desired.

BRIEF DESCRIPTION OF THE DRAWINGS

FIG. 1 (SEQ ID NO: 1 and SEQ ID NO: 2) shows the DNA and deduced amino acid sequence of murine C140 receptor.

FIG. 2 (SEQ ID NO: 3 and SEQ ID NO: 4) shows the DNA and deduced amino acid sequence of human C140 receptor.

FIG. 3 (SEQ ID NO: 5 and SEQ ID NO: 6) shows a comparison of amino acid sequences for the human C140 receptor and murine C140 receptor.

FIG. 5 (SEQ ID NO: 5 and SEQ ID NO: 7) shows a comparison of amino acid sequences for the mouse C140 receptor and the human thrombin receptor.

FIG. 8 (Parts a–b) shows blood vessel dilation in rat femoral vein induced by a C140 receptor agonist peptide.

FIG. 9 (Parts a–c) shows the results of an assay for activation of the C140 receptor, expressed in frog oocytes, by plasmin, kallikrein, or trypsin.

MODES OF CARRYING OUT THE INVENTION

The characteristics of the C140 receptor elucidated by the invention herein are summarized in FIGS. 1–4. FIG. 1 shows the complete DNA sequence of the clone encoding the murine receptor, along with the deduced amino acid sequence. As used herein, the "C140 receptor" refers to receptor in any animal species corresponding to the murine receptor contained in clone C140 described in Example 1 herein. Using the native DNA encoding the murine form of this receptor, the corresponding receptors in other species, including humans, as illustrated herein, may be obtained. FIG. 2 shows the corresponding DNA and deduced amino acid sequence of the human receptor.

The entire amino acid sequence of the murine receptor contains 395 amino acids, including a 27 amino acid signal peptide which, when cleaved, results in a 368 amino acid mature receptor protein. Similarly, the human receptor is encoded by an open reading frame corresponding to 398 amino acids including a probable 29 amino acid signal peptide sequence resulting in a 369 amino acid mature receptor protein, as shown in FIG. 2.

FIG. 3 shows a comparison of the human and murine amino acid sequences; as shown, these sequences exhibit a high degree of homology.

Figure 4:
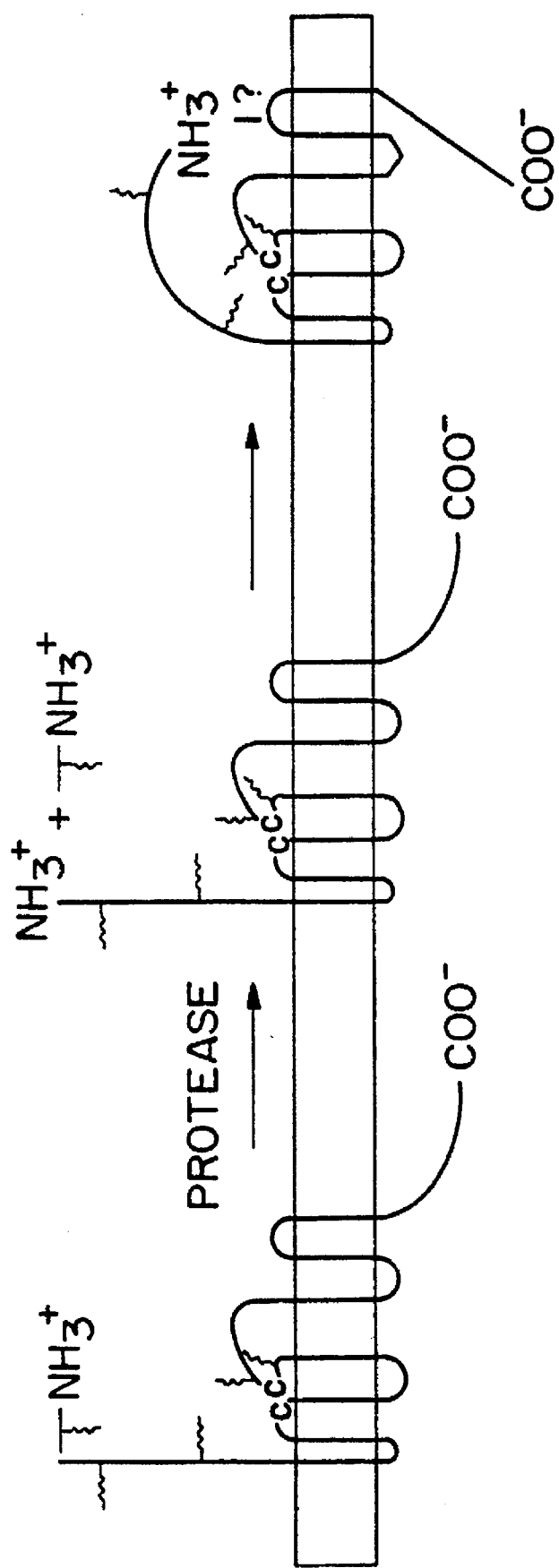
FIG. 4 shows a proposed model of C140 receptor activation based on the deduced amino acid sequence.

Hydrophobicity/hydrophilicity plots of the sequences shown in FIGS. 1 and 2 indicate that the mature C140 receptor is a member of the 7-transmembrane domain receptor family whose effect on the cell is mediated by G-protein. The mature C140 receptor has a relatively long extracellular amino acid extension containing several consensus sites for asparagine-linked glycosylation. It also contains a conserved asparagine in the first transmembrane region, the motif Leu-Ala-X-X-Asp in the second transmembrane region, a Trp in the fourth transmembrane region and a carboxy terminal tail which contains multiple serine and threonine residues. A proposed model of the in situ receptor is shown in FIG. 4.

Referring to FIG. 5, similarities to the thrombin receptor are readily seen. FIG. 5 compares the amino acid sequence of murine C140 with that of thrombin receptor. It is known that the thrombin receptor is activated by proteolytic cleavage of the Arg-Ser bond at positions 41 and 42, which releases an activation peptide that permits refolding of the receptor and activation via the newly created amino terminus. In an analogous manner, the C140 receptor is activated by cleavage of the Arg-Ser bond at positions 34 and 35, also liberating an activation peptide extending from position 1 of the putative mature protein to the cleavage site. It is believed that Arg-28 is the amino terminal amino acid residue of the mature protein, so the activation peptide has the sequence RNNSKGR (SEQ ID NO: 8). This peptide could thus be used as an index for activation of C140 receptor. In any event, the precise location of the N-terminus of the mature protein is unimportant for the design of agonists or antagonists. The activation peptide is likely to be freely filtered by the kidney and possibly concentrated in the urine and can be used as an index to activation of the C140 receptor.

Release of the activation peptide permits refolding of the receptor protein to activate the receptor. This is shown schematically in FIG. 4, which also shows that the conformational changes resulting from the liberation of the activation peptide and refolding results in an intracellular conformational change of the receptor. This hypothesis is confirmed by the finding that the C140 receptor can be activated by a peptide mimicking the new amino terminus created by the activation. Accordingly, mimics of the N-terminus of the new amino terminus on the activated receptor behave as agonists therefor. The importance of the first five amino acids in the newly created amino terminus in the receptor for receptor activation has also been confirmed hereinbelow.

Based on this information, and by analogy with the mechanisms underlying trypsinogen activation to trypsin and activation of the thrombin receptor, it appears that the positively charged amino group on serine that is newly exposed when the ligand cleaves the receptor plays an important role in receptor activation. Peptides based on the agonist peptide sequence that bind the C140 receptor, but which are modified to be lacking the free α-amino group can function as antagonists of this receptor. Thus, modifications of the agonist peptides which lack the capacity for specific activating interaction serve as C140 receptor antagonists.

COMPOUNDS OF THE INVENTION

The nomenclature used to describe the peptide compounds of the invention follows the conventional practice where the N-terminal amino group is assumed to be to the left and the carboxy group to the right of each amino acid residue in the peptide. In the formulas representing selected specific embodiments of the present invention, the amino- and carboxy-terminal groups, although often not specifically shown, will be understood to be in the form they would assume at physiological pH values, unless otherwise specified. Thus, the N-terminal H$^+_2$ and C-terminal O$^-$ at physiological pH are understood to be present though not necessarily specified and shown, either in specific examples or in generic formulas. Free functional groups on the side chains of the amino acid residues can also be modified by amidation, acylation or other substitution, which can, for example, change the solubility of the compounds without affecting their activity.

In the peptides shown, each gene-encoded residue, where appropriate, is represented by a single letter designation, corresponding to the trivial name of the amino acid, in accordance with the following conventional list:

| Amino Acid | One-Letter Symbol | Three-letter Symbol |
| --- | --- | --- |
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |

-continued

| Amino Acid | One-Letter Symbol | Three-letter Symbol |
|---|---|---|
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The amino acids not encoded genetically are abbreviated as indicated in the discussion below.

In the specific peptides shown in the present application, the L-form of any amino acid residue having an optical isomer is intended unless the D-form is expressly indicated by a dagger superscript (†).

The compounds of the invention are peptides which are partially defined in terms of amino acid residues of designated classes. Amino acid residues can be generally subclassified into four major subclasses as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH.

Basic: The residue has a positive charge due to association with H ion at physiological pH and the residue is attracted by aqueous solution so as to seek the surface positions in the conformation of a peptide in which it is contained when the peptide is in aqueous medium at physiological pH.

Neutral/nonpolar: The residues are not charged at physiological pH and the residue is repelled by aqueous solution so as to seek the inner positions in the conformation of a peptide in which it is contained when the peptide is in aqueous medium. These residues are also designated "hydrophobic" herein.

Neutral/polar: The residues are not charged at physiological pH, but the residue is attracted by aqueous solution so as to seek the outer positions in the conformation of a peptide in which it is contained when the peptide is in aqueous medium.

It is understood, of course, that in a statistical collection of individual residue molecules some molecules will be charged, and some not, and there will be an attraction for or repulsion from an aqueous medium to a greater or lesser extent. To fit the definition of "charged," a significant percentage (at least approximately 25%) of the individual molecules are charged at physiological pH. The degree of attraction or repulsion required for classification as polar or nonpolar is arbitrary and, therefore, amino acids specifically contemplated by the invention have been classified as one or the other. Most amino acids not specifically named can be classified on the basis of known behavior.

Amino acid residues can be further subclassified as cyclic or noncyclic, and aromatic or nonaromatic, self-explanatory classifications with respect to the side chain substituent groups of the residues, and as small or large. The residue is considered small if it contains a total of 4 carbon atoms or less, inclusive of the carboxyl carbon. Small residues are, of course, always nonaromatic.

For the naturally occurring protein amino acids, subclassification according to the foregoing scheme is as follows.

Acidic: Aspartic acid and Glutamic acid;

Basic/noncyclic: Arginine, Lysine;

Basic/cyclic: Histidine;

Neutral/polar/small: Glycine, serine, cysteine;

Neutral/nonpolar/small: Alanine;

Neutral/polar/large/nonaromatic: Threonine, Asparagine, Glutamine;

Neutral/polar/large aromatic: Tyrosine;

Neutral/nonpolar/large/nonaromatic: Valine, Isoleucine, Leucine, Methionine;

Neutral/nonpolar/large/aromatic: Phenylalanine, and Tryptophan.

The gene-encoded secondary amino acid proline, although technically within the group neutral/nonpolar/large/cyclic and nonaromatic, is a special case due to its known effects on the secondary conformation of peptide chains, and is not, therefore, included in this defined group.

Certain commonly encountered amino acids, which are not encoded by the genetic code, include, for example, beta-alanine (beta-Ala), or other omega-amino acids, such as 3-amino propionic, 2,3-diamino propionic (2,3-diaP), 4-amino butyric and so forth, alpha-aminisobutyric acid (Aib), sarcosine (Sat), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), cysteic acid (Cya) 2-naphthylalanine (2-Nal); 1,2,3,4-tetrahydroisoquinoline-3-carboxylic acid (Tic); β-2-thienylalanine (Thi); and methionine sulfoxide (MSO). These also fall conveniently into particular categories.

Based on the above definitions,

Sar, beta-Ala, 2,3-diaP and Aib are neutral/nonpolar/small;

t-BuA, t-BuG, N-MeIle, Nle, Mvl and Cha are neutral/nonpolar/large/nonaromatic;

Orn is basic/noncyclic;

Cya is acidic;

Cit, Acetyl Lys, and MSO are neutral/polar/large/nonaromatic; and

Phg, Nal, Thi and Tic are neutral/nonpolar/large/aromatic.

The various omega-amino acids are classified according to size as neutral/nonpolar/small (beta-Ala, i.e., 3-aminopropionic, 4-aminobutyric) or large (all others).

Other amino acid substitutions of those encoded in the gene can also be included in peptide compounds within the scope of the invention and can be classified within this general scheme according to their structure.

All of the compounds of the invention, when an amino acid forms the C-terminus, may be in the form of the pharmaceutically acceptable salts or esters. Salts may be, for example, $Na^+$, $K^+$, $Ca^{+2}$, $Mg^{+2}$ and the like; the esters are generally those of alcohols of 1–6C.

In all of the peptides of the invention, one or more amide linkages (—CO—NH—) may optionally be replaced with another linkage which is an isostere such as —$CH_2NH$—, —$CH_2S$—, —$CH_2CH_2$, —CH=CH— (cis and trans), —$COCH_2$—, —CH(OH)$CH_2$— and —$CH_2SO$—. This replacement can be made by methods known in the art. The following references describe preparation of peptide analogs which include these alternative-linking moieties: Spatola, A. F., *Vega Data* (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Morley, J. S., *Trends Pharm Sci* (1980) pp. 463–468 (general review); Hudson, D., et al., *Int J Pept Prot Res* (1979) 14:177–185 (—CH$_2$NH—, —CH$_2$CH$_2$—); Spatola, A. F., et al., *Life Sci* (1986) 38:1243–1249 (—CH$_2$—S); Harm, M. M., *J Chem Soc Perkin Trans I* (1982) 307–314 (—CH—CH—, cis and trans); Almquist, R. G., et al., *J Med Chem* (1980) 23:1392–1398 (—COCH$_2$—); Jennings-White, C., et al., *Tetrahedron Lett* (1982) 23:2533 (—COCH$_2$—); Szelke, M., et al., European Application EP 45665 (1982) CA:97:39405 (1982) (—CH(OH)CH$_2$—); Holladay, M. W., et al., *Tetrahedron Lett* (1983) 24:4401–4404 (—C(OH)CH$_2$—); and Hruby, V. J., *Life Sci* (1982) 31:189–199 (—CH$_2$—S—).

A. Agonists

The agonists of the invention comprise a series of peptides of the formula

  (1)

wherein AA$_1$ is a small amino acid or threonine;

AA$_2$ and AA$_3$ are each independently neutral/nonpolar/large/nonaromatic amino acids;

AA$_4$ is a small amino acid;

AA$_5$ is a basic amino acid;

AA$_6$ may be present or absent and, if present, is a neutral/nonpolar/large/nonaromatic amino acid;

AA$_7$ is absent if AA$_6$ is absent and may be present or absent if AA$_6$ is present, and is an acidic amino acid; and Z is a substituent that does not interfere with agonist activity.

The peptide of formula 1 can be extended (shown as included in Z) at the C-terminus (but not the N-terminus) by further amino acid sequence to comprise a noninterfering substituent.

At the C-terminus of the compounds of formula 1, the carboxyl group may be in the underivatized form or may be amidated or may be an ester; in the underivatized form the carboxyl may be as a free acid or a salt, preferably a pharmaceutically acceptable salt.

If the C-terminus is amidated, the nitrogen atom of the amido group, covalently bound to the carbonyl carbon at the C-terminus, will be NR'R', wherein each R' is independently hydrogen or is a straight or branched chain alkyl of 1–6C, such alkyls are 1–6C straight- or branched-chain saturated hydrocarbyl residues, such as methyl, ethyl, isopentyl, n-hexyl, and the like. Representatives of such amido groups are: —NH$_2$, —NHCH$_3$, —N(CH$_3$)$_2$, —NHCH$_2$CH$_3$, —NHCH$_2$CH(CH$_3$)$_2$, and —HHCH$_2$CH(CH$_3$)CH$_2$CH$_3$, among others. Furthermore, either or both R' may in turn optionally be substituted by one or more substituents such as, for example, —OR', —NR'R', halo, —NR'CNR'NR'R' and the like, wherein each R' is as independently defined above. Thus, Z may be —OH, or an ester (OR') or salt forms thereof, or —NR'R' wherein R' is as above defined.

Preferred embodiments of AA$_1$ are Ser on 2,3-diaminopropionyl (2,3-diaP). Preferred embodiments of AA$_2$ and AA$_3$ are Val, Ile, Cha and Leu. Preferred embodiments for the residues in the remainder of the compound of formula (1) are those wherein AA$_4$ is Gly, AA$_5$ is Lys, Arg or Har, AA$_6$, if present, is Val, Ile, Cha or Leu, and AA$_7$, if present, is Asp or Glu. Particularly preferred are compounds of formula (1) which are selected from the group consisting of SLIGRLETQPPIT (SEQ ID NO: 32), SLIGRLETQPPI (SEQ ID NO: 33), SLIGRLETQPP (SEQ ID NO: 34), SLIGRLETQP (SEQ ID NO: 35), SLIGRLETQ (SEQ ID NO: 36), SLIGRLET (SEQ ID NO: 37), SLIGRLE (SEQ ID NO: 38), SLIGRL (SEQ ID NO: 39), SLIGR (SEQ ID NO: 40), SLLGKVDGTSHVT (SEQ ID NO: 41), SLLGKVDGTSHV (SEQ ID NO: 42), SLLGKVDGTSH (SEQ ID NO: 43), SLLGKVDGTS (SEQ ID NO: 44), SLLGKVDGT (SEQ ID NO: 45), SLLGKVDG (SEQ ID NO: 46), SLLGKVD (SEQ ID NO: 47), SLLGKV (SEQ ID NO: 48), SLLGK (SEQ ID NO: 49), S(Cha) IGR (SEQ ID NO: 50), S(Cha)LGK (SEQ ID NO: 51), (2,3-diaP)-IGR (SEQ ID NO: 52), (2,3-diaP)LLGK (SEQ ID NO: 53), SLLGKR-NH$_2$ (SEQ ID NO: 54), SLIGRR-NH$_2$ (SEQ ID NO: 55), S (Cha)LGKK-NH$_2$ (SEQ ID NO: 56), S (Cha) IGRK-NH$_2$ (SEQ ID NO: 57), (2,3-diaP)-LIGRK-NH$_2$ (SEQ ID NO: 58), (2,3-diaP)-LLGKK-NH$_2$ (SEQ ID NO: 59) and the amidated forms thereof.

B. Antagonists

Compounds of the invention which interfere with activities mediated by the C140 receptor include modified agonist peptides lacking the N-terminal serine residue; and antibodies which are immunoreactive with various critical positions on the C140 receptor.

Peptide Antagonists

The antagonists of the first group-modified agonists—can be represented by the formula:

wherein X is an amino acid residue other than ser, ala, thr, cys, 2,3-diaP or gly or is a desamino or alkylated or acylated amino acid, wherein AA$_2$ and AA$_3$ are each independently neutral/nonpolar/large/nonaromatic amino acids;

AA$_4$ is a small amino acid;

AA$_5$ is a basic amino acid;

AA$_6$ may be present or absent and, if present, is a neutral/nonpolar/large/nonaromatic amino acid;

AA$_7$ is absent if AA$_6$ is absent and may be present or absent if AA$_6$ is present, and is an acidic amino acid; and Z is a substituent that does not interfere with agonist activity.

Preferred acyl groups are of the formula RCO— wherein R represents a straight or branched chain alkyl of 1–6C. Acetyl is particularly preferred.

Preferred embodiments of X include residues of 3-mercaptopropionic acid (Mpr), 3-mercaptovaleric acid (Mvl), 2-mercaptobenzoic acid (Mba) and S-methyl-3-mercaptopropionic acid (SMeMpr). Preferred embodiments for AA$_2$ through AA$_7$ are as described for the agonists above; Z is also as thus described.

Particularly preferred among the antagonist peptides of this class are those selected from the group consisting of Mpr-LLGK (SEQ ID NO: 9), Mpr-LIGR (SEQ ID NO: 10), Mpr-(Cha)LKG (SEQ ID NO: 11), Mpr-(Cha) IGR (SEQ ID NO: 12), Mpr-LLGKK-NH$_2$ (SEQ ID NO: 13), Mpr-LIGRK-NH$_2$ (SEQ ID NO: 14), Mpr-LIGRKETQP-NH$_2$ (SEQ ID NO: 15), Mpr-LLGKKDGTS-NH$_2$ (SEQ ID NO: 16), (n-pentyl)$_2$-N-Leu-Ile-Gly-Arg-Lys-NH$_2$ (SEQ ID NO: 17) and (Me-N-(n-pentyl)-Leu-Ile-Gly-Arg-Lys-NH$_2$ (SEQ ID NO: 18).

Antibodies

Antagonists which are antibodies immunoreactive with critical positions of the C140 receptor are obtained by immunization of suitable mammalian subjects with peptides containing as antigenic regions those portions of the C140 receptor intended to be targeted by the antibodies. Critical regions include the region of proteolytic cleavage, the segment of the extracellular segment critical for activation (this includes the cleavage site), and the portions of the sequence which form the extracellular loops, in particular, that region which interacts with the N-terminus of the activated receptor extracellular region. The agonist peptides of the invention may be used as immunogens in this case.

Thus, peptides which contain the proteolytic region, namely, for example, SKGRSLIGRLET (SEQ ID NO: 19), the extracellular loops, such as those including ISY HLH-GNNWVYGEALC (SEQ ID NO: 20); QTIYIPALNIT-TCHDVLPEEVLVGDMFNYFL (SEQ ID NO: 21); and HYFLIKTQRQSHVYA (SEQ ID NO: 22). The agonist peptides described below are also useful as immunogens.

The antibodies are prepared by immunizing suitable mammalian hosts in appropriate immunization protocols using the peptide haptens alone, if they are of sufficient length, or, if desired, or if required to enhance immunogenicity, conjugated to suitable carriers. Methods for preparing immunogenic conjugates with carriers such as BSA, KLH, or other carrier proteins are well known in the art. In some circumstances, direct conjugation using, for example, carbodiimide reagents may be effective; in other instances linking reagents such as those supplied by Pierce Chemical Co., Rockford, Ill., may be desirable to provide accessibility to the hapten. The hapten peptides can be extended at the amino or carboxy terminus with a Cys residue or interspersed with cysteine residues, for example, to facilitate linking to carrier. Administration of the immunogens is conducted generally by injection over a suitable time period and with use of suitable adjuvants, as is generally understood in the art. During the immunization schedule, titers of antibodies are taken to determine adequacy of antibody formation.

While the polyclonal antisera produced in this way may be satisfactory for some applications, for pharmaceutical compositions, use of monoclonal preparations is preferred. Immortalized cell lines which secrete the desired monoclonal antibodies may be prepared using the standard method of Kohler and Milstein or modifications which effect immortalization of lymphocytes or spleen cells, as is generally known. The immortalized cell lines secreting the desired antibodies are screened by immunoassay in which the antigen is the peptide hapten or is the C140 receptor itself displayed on a recombinant host cell. When the appropriate immortalized cell culture secreting the desired antibody is identified, the cells can be cultured either in vitro or by production in ascites fluid.

The desired monoclonal antibodies are then recovered from the culture supernatant or from the ascites supernatant. Fragments of the monoclonals or the polyclonal antisera which contain the immunologically significant portion can be used as antagonists, as well as the intact antibodies. Use of immunologically reactive fragments, such as the Fab, Fab', of F(ab')$_2$ fragments is often preferable, especially in a therapeutic context, as these fragments are generally less immunogenic than the whole immunoglobulin.

The antibodies or fragments may also be produced, using current technology, by recombinant means. Regions that bind specifically to the desired regions of receptor can also be produced in the context of chimeras with multiple species origin.

The antibodies thus produced are useful not only as potential antagonists for the receptor, filling the role of antagonist in the assays of the invention, but are also useful in immunoassays for detecting the activated receptor. As such these antibodies can be coupled to imaging agents for administration to a subject to allow detection of localized antibody to ascertain the position of C140 receptors in either activated or unactivated form. In addition, these reagents are useful in vitro to detect, for example, the successful production of the C140 receptor deployed at the surface of the recombinant host cells.

Preparation of Peptide Agonists and Antagonists

The peptide agonists and antagonists of the invention can be prepared using standard solid phase (or solution phase) peptide synthesis methods, as is known in the art. In addition, the DNA encoding these peptides may be synthesized using commercially available oligonucleotide synthesis instrumentation and produced recombinantly using standard recombinant production systems. The production using solid phase peptide synthesis is necessitated if non-gene-encoded amino acids are to be included.

Recombinant Production of C140 Receptor for Use in Assays

The invention provides recombinant materials for the production of C140 receptor for display on the surface of recombinant cells. Production of the receptor using these recombinant methods provides a useful reagent to determine the ability of a candidate drug to bind to, to activate, or to antagonize the C140 receptor. Determination of these properties is essential in evaluating the specificity of drugs intended for binding other related receptors.

For this recombinant production, a DNA sequence encoding the C140 receptor, such as those set forth in FIGS. 1 and 2, or their substantial equivalents or their degenerate analogs, is prepared either by retrieval of the native sequence, as set forth below, or by using substantial portions of the known native sequence as probe, or can be synthesized de novo using standard procedures. The DNA is ligated into expression vectors suitable for the desired host and transformed into compatible cells. The cells are cultured under conditions which favor the expression of the C140 receptor encoding gene and the cells displaying the receptor on the surface are harvested for use in the assays.

The host cells are typically animal cells, most typically mammalian cells. In order to be useful in the assays, the cells must have intracellular mechanisms which permit the receptor to be displayed on the cell surface in the configuration shown generally in FIG. 4 herein. If the assay uses cellular response to activated receptor as a detection system, the cells must also contain a G-protein linked mechanism for response to activation of the receptors. Most mammalian and other animal cells fulfill these qualifications.

Particularly useful cells for use in the method of the invention are *Xenopus laevis* frog oocytes, which typically utilize cRNA rather than standard recombinant expression systems proceeding from the DNA encoding the desired protein. Capped RNA is typically produced from linearlized vectors containing DNA sequences encoding the receptor. The reaction is conducted using RNA polymerase and standard reagents. cRNA is recovered, typically using phenol/chloroform precipitation with ethanol and injected into the oocytes.

The animal host cells expressing the DNA encoding the C140 receptor or the cRNA-injected oocytes are then cultured to effect the expression of the encoding nucleic acids so as to produce the C140 receptor displayed in a manner analogous to that shown in FIG. 4 on their surfaces. These cells then are used directly in assays for assessment of a candidate drug to bind, antagonize, or activate the receptor.

Assays

In one type of easily conducted assay, competition of the candidate drug for binding to the receptor with either agonist or known binding antagonist can be tested. In one method, the competing agonist or antagonist may be labeled; the labeled substance known to bind the receptor can, of course, be a synthetic peptide. In one typical protocol, varying concentrations of the candidate are supplied along with a constant concentration of labeled agonist or antagonist and the inhibition of a binding of label to the receptor can be evaluated using known techniques.

In a somewhat more sophisticated approach, the effect of candidate compounds on agonist-induced responses can be measured in the cells recombinantly expressing the C140 receptor as described below. Assay systems for the effect of activation of receptor on these cells include calcium mobilization and voltage clamp which are described herein in further detail. These assays permit an assessment of the effect of the candidate drug on the receptor activity rather than simply ability to bind to the receptor.

Agonist-induced increases in $^{45}$Ca release by oocytes expressing cRNA encoding C140 receptor or other recombinant cells producing C140 receptor are assessed by published techniques (Williams, J. A., et al., *Proc Natl Acad Sci USA* (1988) 85:4939–4943). Briefly, intracellular calcium pools are labeled by incubating groups of 30 oocytes in 300 µl calcium-free modified Barth's solution (MBSH) containing 50 µCi $^{45}$CACl$_2$ (10–40 mCi/mg Ca; Amersham) for 4 hours at RT. The labeled oocytes or cells are washed, then incubated in MBSH II without antibiotics for 90 minutes. Groups of 5 oocytes are selected and placed in individual wells in a 24-well tissue culture plate (Falcon 3047) containing 0.5 ml/well MBSH II without antibiotics. This medium is removed and replaced with fresh medium every 10 minutes; the harvested medium is analyzed by scintillation counting to determine $^{45}$Ca released by the oocytes during each 10-minute incubation. The 10-minute incubations are continued until a stable baseline of $^{45}$Ca release per unit time is achieved. Two additional 10-minute collections are obtained, then test medium including agonist is added and agonist-induced $^{45}$Ca release determined.

Using the above assay, the ability of a candidate drug to activate the receptor can be tested directly. In this case, the agonists of the invention are used as controls. In addition, by using the agonist of the invention to activate the recombinant receptor, the effect of the candidate drug on this activation can be tested directly. Recombinant cells expressing the nucleic acids encoding the receptor are incubated in the assay in the presence of agonist with and without the candidate compound. A diminution in activation in the presence of the candidate will indicate an antagonist effect. Conversely, the ability of a candidate drug to reverse the antagonist effects of an antagonist of the invention may also be tested.

In an alternative to measuring calcium mobilization, the voltage clamp assay can be used as a measure for receptor activation. Agonist-induced inward chloride currents are measured in voltage-clamped oocytes expressing C140 receptor encoding cRNA or cells expressing DNA from recombinant expressions systems essentially as previously described (Julius, D., et al, *Science* (1988) 241:558–563) except that the single electrode voltage-clamp technique is employed.

Detection of Activated Receptors

In one embodiment, the availability of the recombinant C140 receptor protein permits production of antibodies which are immunospecific to the activated form of the receptor which can then be used for diagnostic imaging of activated receptors in vivo. These antibodies are produced either to the activated form of the receptor produced recombinantly, or to the peptide representing the "new amino terminal" peptide described herein. The resulting antibodies, or the immunospecific fragments thereof, such as the Fab, Fab', Fab'$_2$ fragments are then conjugated to labels which are detected by known methods, such as radiolabels including technetium$^{99}$ and indium$^{111}$ or other radioactive labels as is known in the art. When injected in vivo, these antibodies home to the sites of activated receptor, thus permitting localization of areas containing activated receptors.

In another embodiment, the presence of the activation peptide in body fluids or in culture media can be detected and measured. Antibodies are made to the activation peptide as described above and can be employed in standard ELISA or RIA assays to detect excess amounts of the activation peptide in, for example, urine.

Administration of Agonists and Antagonists as Pharmaceuticals

The peptides of the invention which behave as agonists are administered in conventional formulations for systemic administration as is known in the art. Typical such formulations may be found, for example, in *Remington's Pharmaceutical Sciences*, Mack Publishing Co., Easton Pa., latest edition.

Preferred forms of systemic administration of peptides include injection, typically by intravenous injection. Other injection routes, such as subcutaneous, intramuscular, or intraperitoneal, can also be used. More recently, alternative means for systemic administration of peptides have been devised which include transmucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the patient's condition, and the judgment of the attending physician. Suitable dosage ranges, however, are in the range of 0.1–100 µg/kg of subject. Wide variations in the needed dosage, however, are to be expected in view of the variety of peptides available and the differing efficiencies of various routes of administration. For example, oral administration would be expected to require higher dosages than administration by intravenous injection. Variations in these dosage levels can be adjusted using standard empirical routines for optimization as is well understood in the art.

As shown hereinbelow, the agonists of the invention behave as antihypotensives; antagonists have the opposite effect. Thus, patients whose blood pressure needs to be raised or lowered benefit by the administration of the suitable peptide.

The following examples are intended to illustrate but not to limit the invention.

EXAMPLE 1

Isolation of the Gene Encoding Murine C140 Receptor

A mouse cosmid genomic library (obtained from Dr. R. A. Wetsel, Washington University School of Medicine, St. Louis, Mo. and described in Wetsel, R. A. et al., *J Biol Chem* (1990) 265:2435–2440) was screened with two $^{32}$P-labeled oligonucleotides corresponding to bp 190–249 and 742–801, respectively, of the bovine substance K receptor cDNA (Masu, Y. et al., *Nature* (1987) 329:836–838). The hybridization conditions are 5×SSC, 5×Denhardt's, 0.1% SDS, 0.1 mg/ml sperm DNA, $10^6$ cpm/ml of labeled oligonucleotides, 60° C. overnight, followed by washing with 1×SSC, 0.1% SDS at 60° C.

In one of the clones isolated (C140) the hybridizing region was localized to a 3.7 kb PstI fragment. This fragment was subcloned into the commercially available pBluescript vector. The hybridizing and adjacent regions were sequenced in both orientations by the Sanger chain termination method. FIG. 1 shows both the nucleotide sequence and the deduced amino acid sequence of the mouse C140 receptor. The tentative signal sequence (SP) and the seven transmembrane regions are overlined, potential asparagine-linked glycosylation sites are marked with bold arrows, and the putative protease receptor cleavage site at Arg34-Ser35 is marked with an open arrow.

EXAMPLE 2

Isolation of the Gene Encoding Human C140 Receptor

The availability of genomic DNA encoding the mouse protease C140 receptor permitted the retrieval of the corresponding human gene. A human genomic library cloned in the vector EMBL3 was screened at exactly the conditions in Example 1 using the entire coding region of the murine clone as a probe. The recovered human gene including the DNA sequence and the deduced amino acid sequence are shown in FIG. 2. The human gene lacks introns in the coding region, as does the mouse gene.

EXAMPLE 3

Comparison of Related G-Protein Receptors

As shown in FIG. 3, the deduced amino acid sequence of the human protease C140 receptor shows extensive similarity (>90%) to the mouse sequence.

FIG. 5 shows an amino acid sequence alignment between the mouse C140 receptor and the related G-protein receptor human thrombin receptor Vu, T. et al., *Cell* (1991) 64:1057–1068. The tentative signal sequences (SP), transmembrane regions, and protease cleavage sites are marked.

EXAMPLE 4

Activation of Protease C140 Receptor in Oocytes

Both native and mutant C140 receptors were produced in oocytes and activated with a peptide mimicking the new amino-terminus", or by the proteolytic enzyme trypsin (which cleaves the extracellular region). Native receptors were produced by cloning the coding region of the receptor gene, using the polymerase chain reaction, into the expression vector pSG-5 (Green, S. et al., *Nucleic Acid Res* (1988) 16:369). The orientation and integrity of the cloned coding region was verified by determining the nucleotide sequence with the Sanger chain-termination method. Site-directed mutagenesis was employed to construct mutant receptors in the pSG-5. Three mutant receptors were made, in which serine-35 was replaced with proline, arginine, and histidine, respectively. The nucleotide sequences of the three mutants was verified as above.

In order to produce the receptor at the surface of oocytes, cRNA encoding the receptor was produced as follows. pSG-5 C140 plasmid DNA was made linear by digestion with XbaI, and capped cRNA was produced in vitro using T7 RNA polymerase (Krieg and Melton, *Meth Enzymol* (1987) 155:397–415.

Oocytes from *Xenopus laevis* were harvested and prepared using published techniques (Coleman, A., in Hames, B. D., and Higgins, S. J., eds, *Transcription and Translation: A Practical Approach*, IRL Press, pp. 271–302; Williams, J. A., et al. *Proc Natl Acad Sci USA* (1988) 85:4939–4943]. To remove follicular cells, oocytes were incubated for 1.5 h with shaking in calcium-free Barth's containing 2 mg/ml each of collagenase 1A and hyaluronidase 1S. The oocytes were then washed five times in regular Barth's and incubated at 18° C. in Barth's medium containing 100 U/ml penicillin, 100 µg/ml streptomycin, and 2.5 mM sodium pyruvate. Stage V oocytes were selected and injected with 30 nl of cRNA (0.33 µg/µl water) or water alone, and then incubated with 0.25 ml of medium in groups of four/well in a 96-well culture plate. After 36 hours the oocytes were incubated with $^{45}$Ca (250 µCi/ml). After 12 h incubation the oocytes were washed and 0.2 ml of medium added and replaced every five-minutes. The harvested medium was analyzed by scintillation counting. After five replacements to determine the baseline release of $^{45}$Ca, test medium with the agonist, e.g. SLIGRL SEQ ID NO: 23, was added and the evoked $^{45}$Ca-release determined.

Oocytes were injected with capped cRNA (ca 10 ng) encoding wild-type mouse C140 receptor (WT) or either of the three mutant receptors 35Pro, 35Arg and 35His. After 36 hours, cRNA-injected and control water-injected, oocytes were loaded with $^{45}$Ca, and 12 hours thereafter peptide or trypsin-induced $^{45}$Ca release were determined as described above. The peptide SLIGRL was added at 100 µM, and trypsin at 300 pM. The stimulation with the peptide was done on the same group of oocytes after the stimulation with trypsin. The data shown in Table 1 represent the mean of three replicate determinations, and denotes the increase compared to oocytes injected with water.

TABLE 1

| Receptor | Agonist | Fold increase in $^{45}$Ca |
|---|---|---|
| WT | Trypsin | 6.6 |
| 35Pro | Trypsin | 0 |
| 35Arg | Trypsin | 0 |
| 35His | Trypsin | 0 |
| WT | SLIGRL (SEQ ID NO:23) | 11 |
| 35Pro | SLIGRL (SEQ ID NO:23) | 23 |
| 35Arg | SLIGRL (SEQ ID NO:23) | 15 |
| 35His | SLIGRL (SEQ ID NO:23) | 23 |

As shown in Table 1, the agonist peptide SLIGRL SEQ ID NO: 23 was able to activate both the wild-type and mutated receptors. On the other hand, trypsin, which can activate only by cleavage of the extracellular domain, is able only to activate the wild-type receptor.

EXAMPLE 5

Activation of the C140 Receptor by Different Agonist Peptides

Various peptides were tested at 100 µM in the assay above using wild-type mouse C140 receptor, expressed in oocytes. The results are shown in Table 2.

TABLE 2

| Peptide | Fold Increase in $^{45}$Ca |
|---|---|
| SLIGRL (SEQ ID NO:23) | 15 |
| SLIGRA (SEQ ID NO:24) | 8.5 |

TABLE 2-continued

| Peptide | Fold Increase in $^{45}$Ca |
| --- | --- |
| SLIGAL (SEQ ID NO:25) | 0 |
| SLIARL (SEQ ID NO:26) | 4.3 |
| SLAGRL (SEQ ID NO:27) | 0 |
| SAIGRL (SEQ ID NO:28) | 0 |
| ALIGRL (SEQ ID NO:29) | 1.3 |
| SFFLRW (SEQ ID NO:30) | 1.7 |

The "native" peptide SLIGRL (SEQ ID NO: 23) is most effective; replacing L at position 6 with alanine lowers but does not destroy activity. Positions 2 and 3 are more sensitive. Position 1 tolerates substitution with alanine but decreases the activity by a factor of 10; the activity of this agonist is comparable to the analogous thrombin receptor agonist SFFLRW (SEQ ID NO: 30).

EXAMPLE 6

Expression of C140 Receptor in Various Tissues

Poly(A)+RNA was prepared from mouse tissues, resolved on a 1.2% agarose gel containing 50% formamide and blotted onto Hybond C extra membrane (Amersham). The blot was hybridized with a $^{32}$P-labeled "random priming probe" directed against the whole coding region of murine C140 receptor. The probe was hybridized at 42° C. for 48 hr then successively washed at 20° C. in 1×SSC, 0.1% SDS twice, 5 min each time, then at 65° C. in 1×SSC, again twice for 20 min each time, and then 0.1×SSC, 0.1% SDS twice for 20 min each time. The resulting membrane was autoradiographed for 5 days at −80° C. with an intensifying screen.

Figure 6:
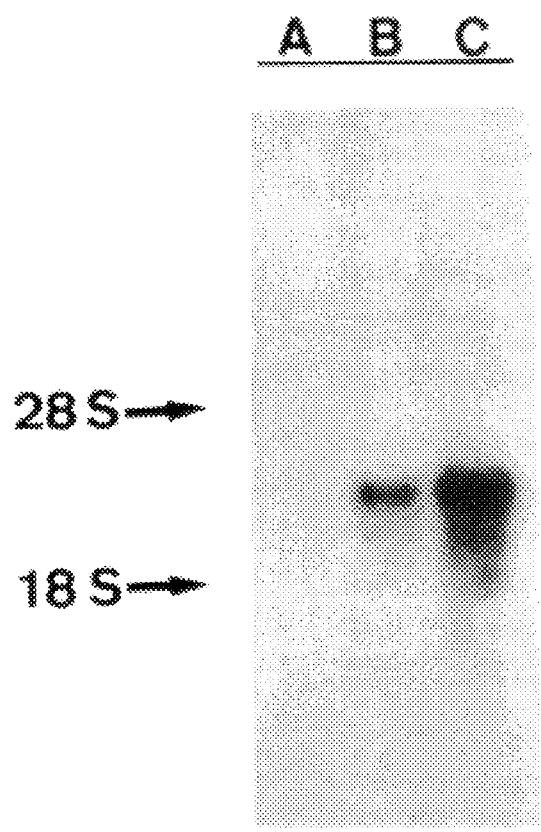
FIG. 6 shows the results of Northern Blot to detect the presence of mRNA encoding C140 receptor in various mouse tissues.

The results, shown in FIG. 6 indicate that kidney and small intestine, but not spleen, contain mRNA encoding C140. In FIG. 6, where each lane contains 10 μg RNA, lane A is derived from spleen, lane B from kidney and lane C from small intestine.

EXAMPLE 7

Determination of Hypotensive Activity of C140 Agonists

The C140 agonist SLIGRL (SEQ ID NO: 23) was injected in 0.2 ml buffer at various concentrations into rat femoral vein and the arterial pressure was monitored. The results of various concentrations are shown in FIG. 7.

Figure 7:
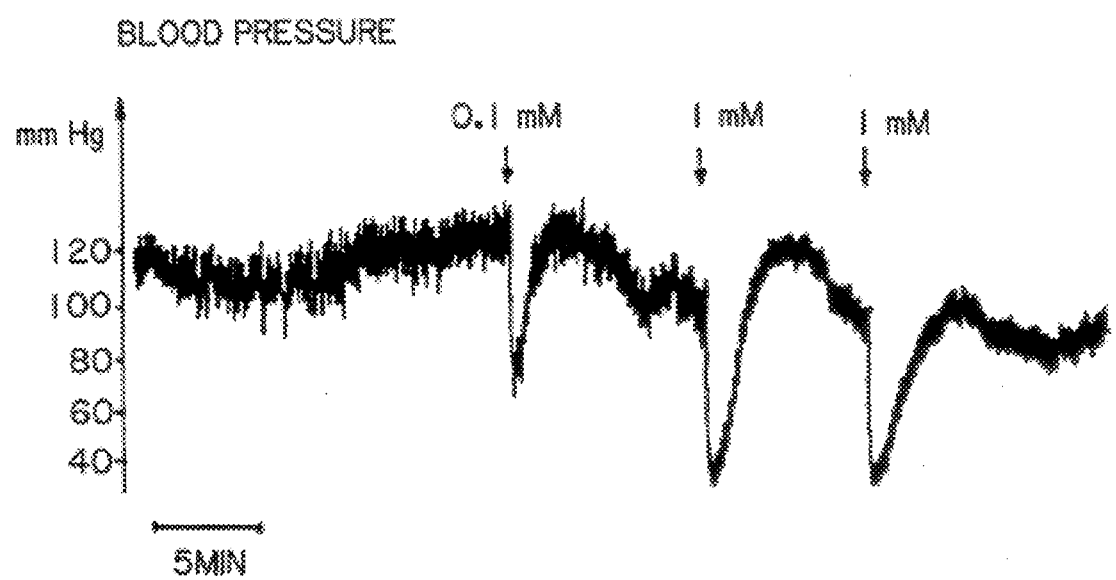
FIG. 7 shows a trace of blood pressure demonstrating the in vivo hypotensive effect of a C140 agonist peptide.

The trace in FIG. 7 shows that even at 0.1 mM an appreciable decrease in blood pressure occurred; larger decreases were observed at 1 mM concentration.

This effect was also shown by observing vasodilation as a result of stimulation of the rat femoral vein with the above agonist. Adult Sprague-Dawley rats were killed by exsanguination during diethylether anesthesia and the femoral vein was removed and dissected free from fat and connective tissue. Circular preparations of the vein were mounted in an organ bath (5 ml) on two L-formed metal holders (0.2 mm diameter). One of the metal holders was screwed into one of the levers of a Grass FTO C force displacement transducer. The bathing liquid was Kreb's Ringer solution containing 118 mM NaCl, 4.7 mM KCl, 2.5 mM $CaCl_2$, 1.2 mM $MgSO_4$, 24.8 mM $NaHCO_3$, 1.2 mM $KH_2PO_4$ and 5.6 mM glucose. The bathing fluid was continuously treated with 88.5% oxygen-11.5% $CO_2$; the temperature was held at 37° C. The endothelium was removed by bubbling $CO_2$ through the vessels. The basal tension was between 7.5 and 12 mN. The preparations were equilibrated for at least 1 hr before application of agonist and control substances.

Figure 8A:
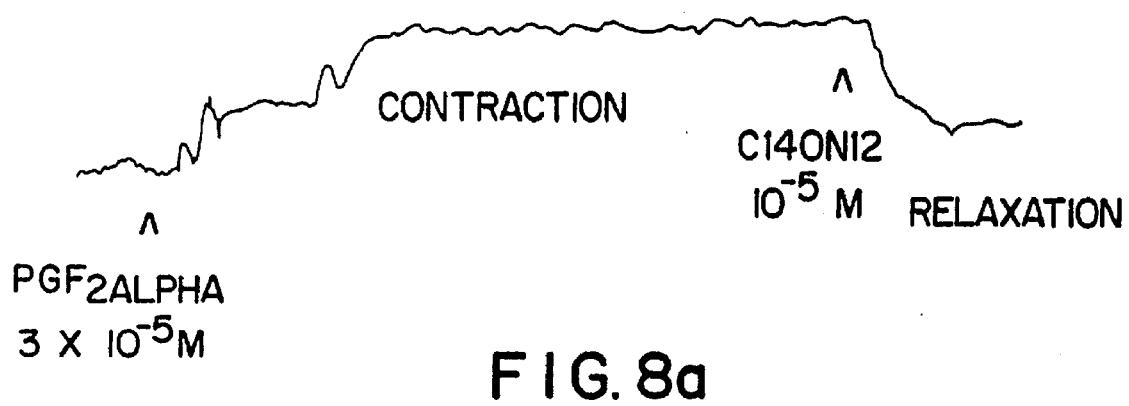
FIG. 8a shows these results in the immobilized vein.
Figure 8B:
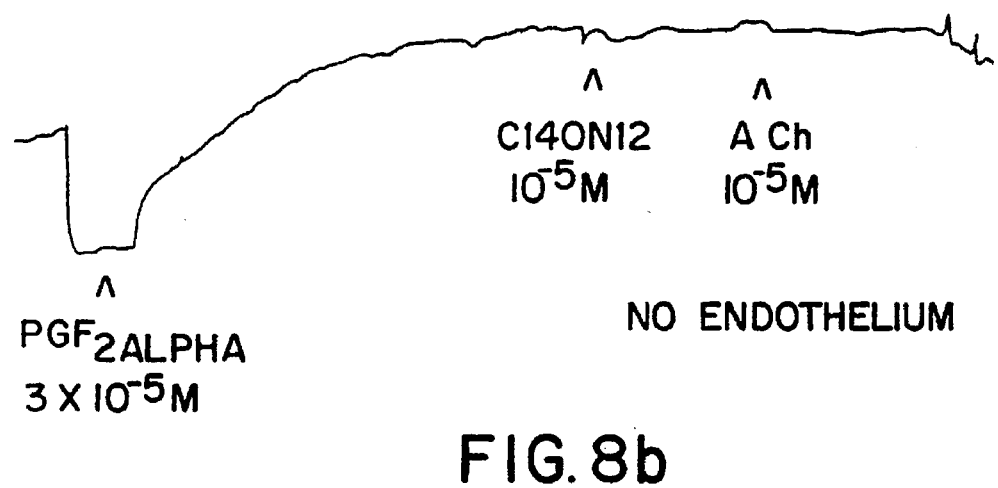
FIG. 8b shows these results for the immobilized vein depleted of endothelial cells.

The results of these determinations are shown in FIG. 8a and 8b. As shown in FIG. 8a, contraction induced by application of $PGF_{2\alpha}$ at $3\times10^{-5}$M is relaxed by administration of $10^{-5}$M agonist. The results in FIG. 8a were obtained using the vein with the endothelium still present.

In FIG. 8b, the endothelium has been removed. In an analogous experiment, the contraction induced by $3\times10^{-5}$M $PGF_{2\alpha}$ is not counteracted by $10^{-5}$M agonist or by $10^{-5}$M acetylcholine.

EXAMPLE 8

Activation of Recombinant C140 Receptor by Plasmin and Kallikrein

Figure 9A:
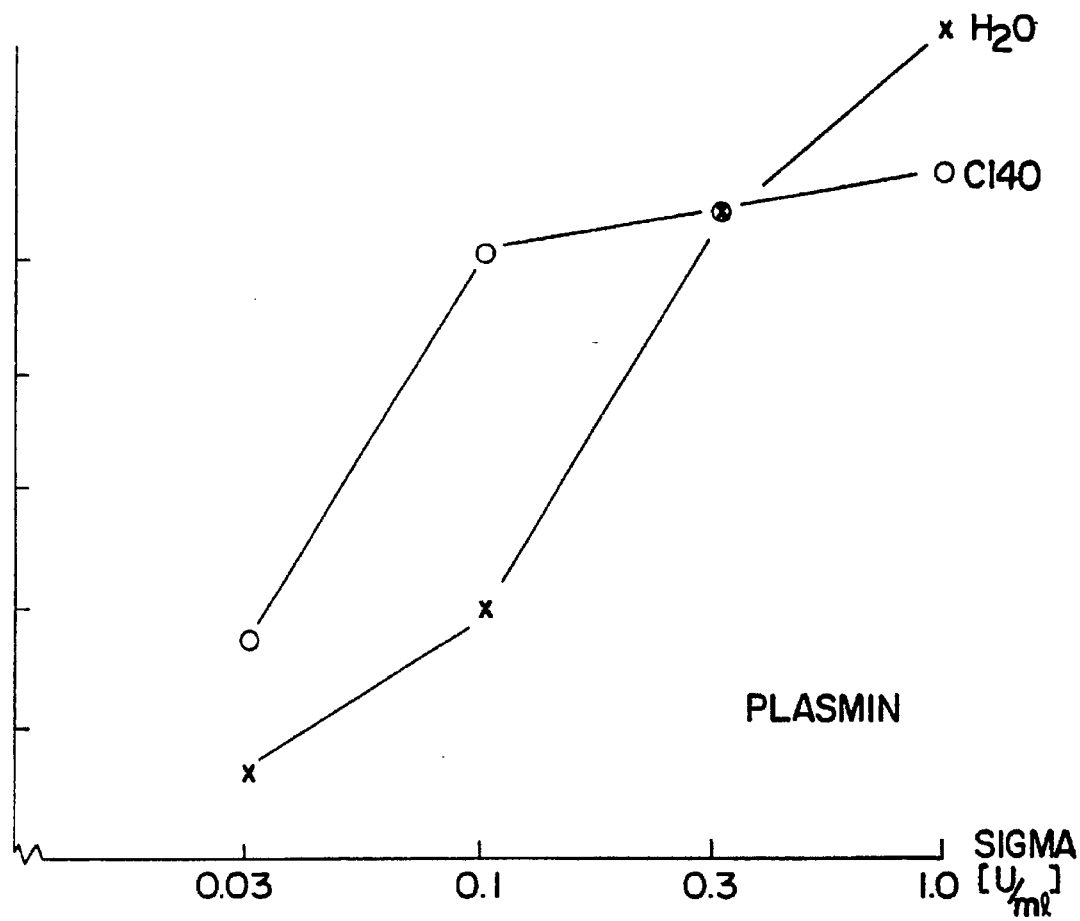
FIG. 9a shows the results for plasmin.
Figure 9B:
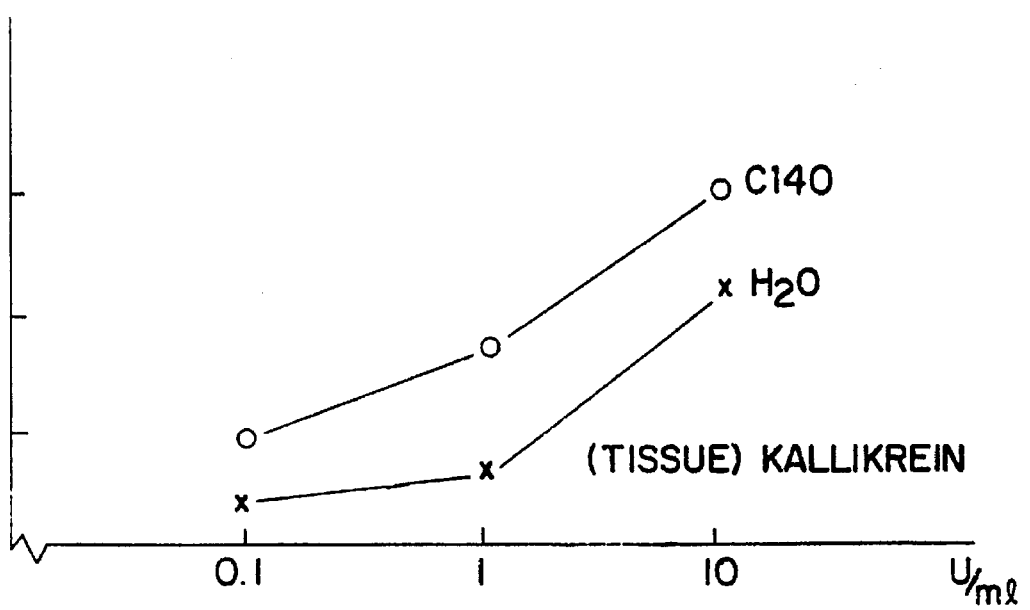
FIG. 9b shows the results for kallikrein.
Figure 9C:
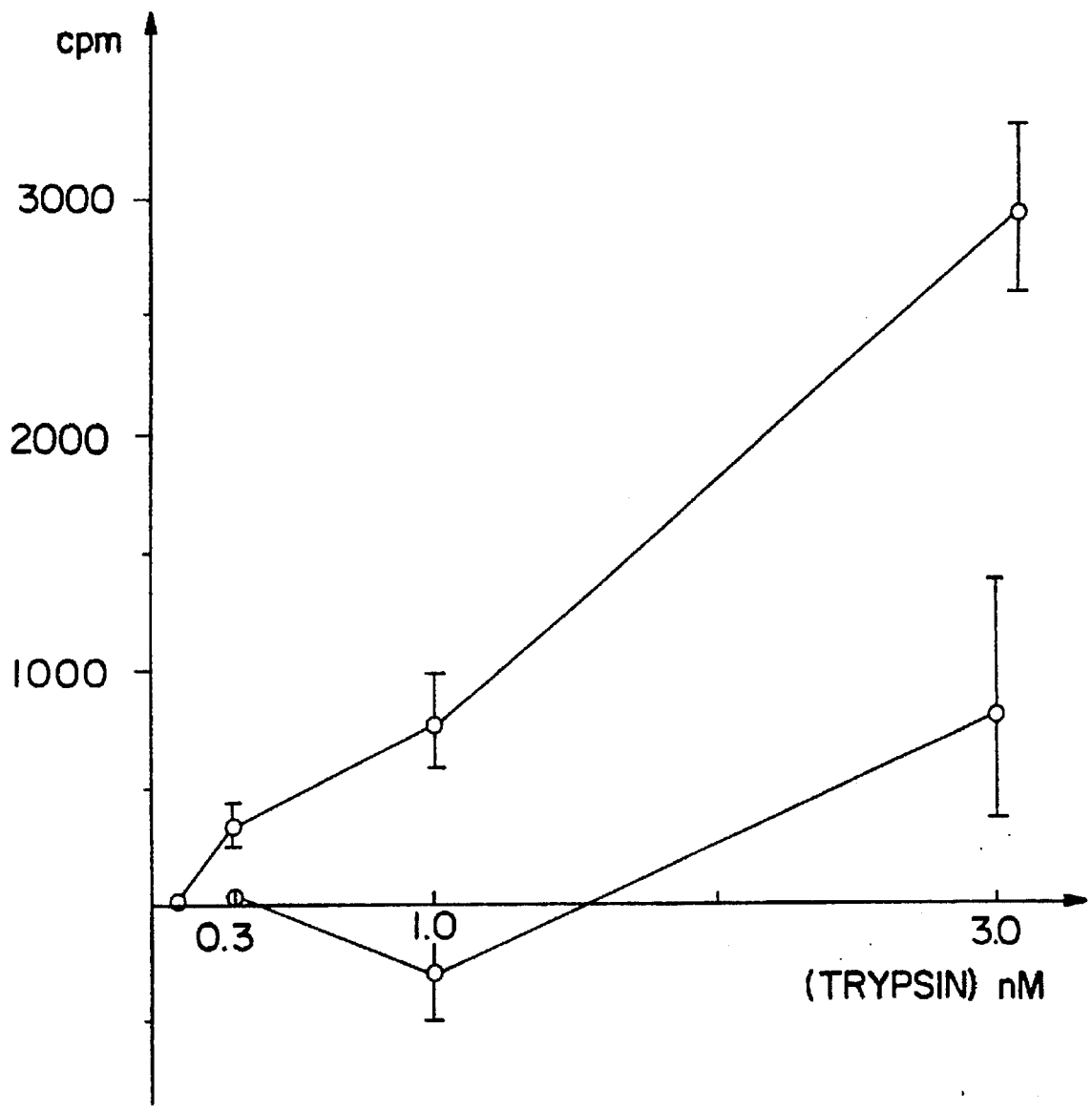
FIG. 9c shows the results for trypsin.

FIGS. 9a and 9b show the ability of plasmin and kallikrein respectively to activate oocytes injected with C140 cRNA (open circles) or water (crosses) as control. FIG. 9c shows the ability of trypsin to activate frog oocytes injected with C140 receptor cRNA (filled circles) or substance K receptor cRNA (open circles). Trypsin clearly has a differential effect on the C140 receptor-injected oocytes.

We claim:

1. A DNA molecule comprising an expression system which, when introduced into a recombinant host, produces the C140 receptor at the cell surface of the host, which expression system comprises a DNA sequence encoding the C140 receptor operably linked to a control sequence heterologous to said encoding DNA and operable in said host cell.

2. A recombinant cell into which the expression system of claim 1 has been introduced.

3. A method of using the molecule of claim 1 to produce cells that contain C140 receptor deployed at their surface, which method comprises culturing the cells of claim 2 under conditions which effect the expression of the DNA encoding the C140 receptor.

4. The cell of claim 2 which is a mammalian somatic cell.

5. A cRNA molecule that encodes the C140 receptor.

6. Recombinant oocytes into which the cRNA of claim 5 has been introduced.

7. A method of using the molecule of claim 5 to produce oocytes that contain C140 receptor deployed at their surface, which method comprises culturing the oocytes of claim 6 under conditions which effect the expression of the cRNA encoding the C140 receptor.

* * * * *